(12) United States Patent
Rodgers et al.

(10) Patent No.: US 10,420,918 B2
(45) Date of Patent: Sep. 24, 2019

(54) COMPOSITIONS AND METHODS FOR REDUCING TRAUMATIC EDEMA OF THE CENTRAL NERVOUS SYSTEM

(71) Applicant: THE REGENTS OF THE UNIVERSITY OF CALIFORNIA, Oakland, CA (US)

(72) Inventors: Victor G. J. Rodgers, Riverside, CA (US); Devin Binder, Riverside, CA (US); Devin McBride, Riverside, CA (US); Michael Hsu, Riverside, CA (US); B. Hyle Park, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/539,385

(22) Filed: Nov. 12, 2014

(65) Prior Publication Data

US 2015/0141950 A1    May 21, 2015

Related U.S. Application Data

(63) Continuation of application No. 13/666,773, filed on Nov. 1, 2012, now abandoned.

(60) Provisional application No. 61/555,351, filed on Nov. 3, 2011.

(51) Int. Cl.
*A61M 27/00* (2006.01)
*A61B 5/00* (2006.01)
(Continued)

(52) U.S. Cl.
CPC ......... *A61M 27/002* (2013.01); *A61B 5/4878* (2013.01); *A61L 29/043* (2013.01);
(Continued)

(58) Field of Classification Search
None
See application file for complete search history.

(56) References Cited

U.S. PATENT DOCUMENTS 4,005,012 A    1/1977   Wrasidlo
4,940,617 A *  7/1990   Baurmeister .......... B01D 63/02
                                                          428/113

(Continued)

OTHER PUBLICATIONS

Sannino et al. "Biomedical application of superabsorbent hydrogel for body water elimination in the treatment of edemas", Wiley Periodicals, Inc., 2003.*

(Continued)

*Primary Examiner* — Isis A Ghali
(74) *Attorney, Agent, or Firm* — Knobbe, Martens, Olson & Bear LLP

(57) ABSTRACT

The invention provides compositions and methods for the treatment and/or reversal of an edema, e.g., including a central nervous system (CNS) edema, e.g., a brain or a spinal edema, edema in a burned or an injured tissue such as skin, or any tissue edema. In alternative embodiments, the invention provides compositions and methods for a direct treatment and reversal of an edema, e.g., CNS, brain or spinal edema, including a membrane transport device, in vitro and in vivo characterization of edema, and the sensitive early optical detection of the edema, e.g., tissue, CNS or cerebral edema.

14 Claims, 14 Drawing Sheets

(51) Int. Cl.
*A61L 29/04* (2006.01)
*A61L 29/16* (2006.01)
*A61K 38/38* (2006.01)
*A61K 38/40* (2006.01)

(52) U.S. Cl.
CPC ............ *A61L 29/044* (2013.01); *A61L 29/16* (2013.01); *A61B 5/0066* (2013.01); *A61B 5/6868* (2013.01); *A61K 38/38* (2013.01); *A61K 38/40* (2013.01); *A61M 2027/004* (2013.01)

(56) References Cited

U.S. PATENT DOCUMENTS

| | | | | |
|---|---|---|---|---|
| 6,030,358 | A * | 2/2000 | Odland | A61M 1/1678 604/264 |
| 2005/0165342 | A1 * | 7/2005 | Odland | A61M 1/0023 604/5.01 |

OTHER PUBLICATIONS

Zhong et al. "Biomaterial for the central nervous system", J.R.Soc. Interface (2008), 5, 957-975 (Year: 2008).*

Zhang et al. "Three dimensional gelatin and gelatin/hyaluronan hydrogel structure for traumatic brain injury", Journal of Bioactive and Compatible Polymers, vol. 22, Jan. 2007 (Year: 2007).*

McBride, D.W. et al. 2014 "Reduction of Cerebral Edema after Traumatic Brain Injury Using an Osmotic Transport Device" *Journal of Neurotrauma* 31:1948-1954.

Chai, Q. et al. 2017 "Hydrogels for Biomedical Applications: Their Characteristics and the Mechanisms behind Them" *Gels* 3(6): in 15 pages.

* cited by examiner

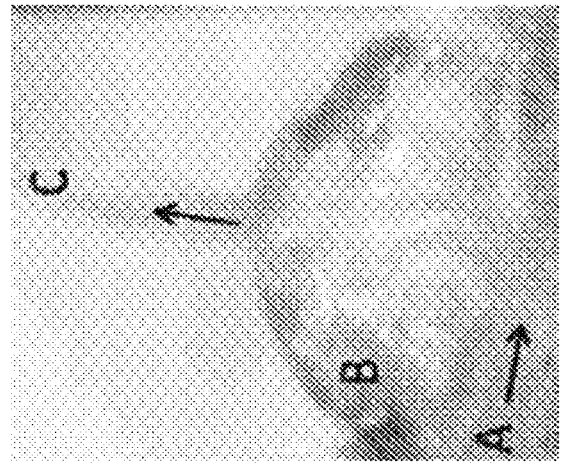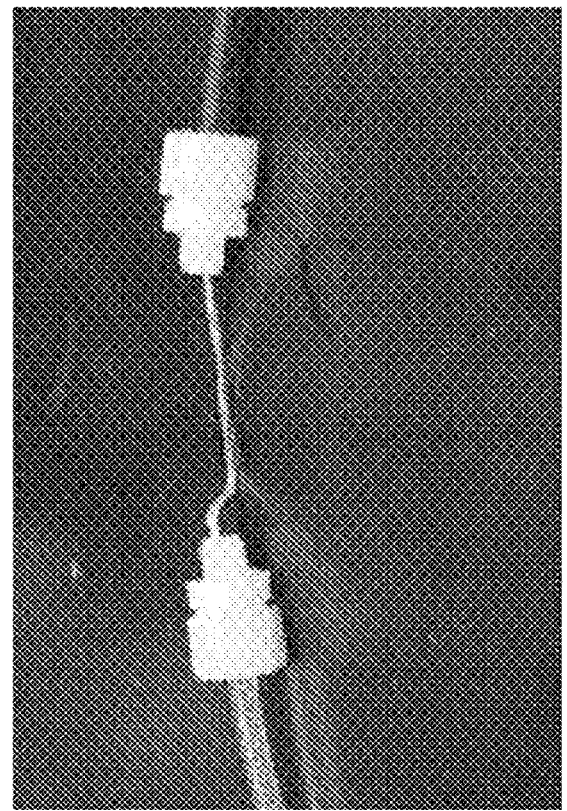
Fig. 9

COMPOSITIONS AND METHODS FOR REDUCING TRAUMATIC EDEMA OF THE CENTRAL NERVOUS SYSTEM

RELATED APPLICATIONS

This application is a continuation of U.S. patent application Ser. No. 13/666,773, filed Nov. 1, 2012, now pending, which claims the benefit of priority under 35 U.S.C. § 119(e) of U.S. Provisional Application No. 61/555,351, filed Nov. 3, 2011. The aforementioned application is expressly incorporated herein by reference in its entirety and for all purposes.

GOVERNMENT RIGHTS

This invention was made with government support under grant number NIH K08 grant NS-059674, awarded by the National Institutes of Health (NIH), and grant number DGE 0903667, awarded by the National Science Foundation. The government has certain rights in the invention.

TECHNICAL FIELD

This invention generally relates to medicine and medical devices. The invention provides compositions and methods for the treatment and/or reversal of an edema, e.g., including a central nervous system (CNS) edema, e.g., a brain or a spinal edema, edema in burned or an injured tissue such as skin, or any tissue edema, injury or insult. In alternative embodiments, the invention provides compositions and methods for a direct treatment and reversal of an edema, e.g., CNS, brain or spinal edema, including a membrane transport device, in vitro and in vivo characterization of edema, and the sensitive early optical detection of the edema, e.g., tissue, CNS or cerebral edema.

BACKGROUND

Cerebral edema, an increase in brain tissue water content, is responsible for significant morbidity and mortality in many different disease states, including traumatic brain injury (TBI), stroke, infection, tumor, and a host of chemical and metabolic intoxications. The two types of cerebral edema are vasogenic edema and cytotoxic (cellular) edema. Vasogenic edema is characterized by the disruption of the blood-brain barrier (BBB) and may be caused by direct injury or by breakdown of the BBB (e.g., by tumors). BBB disruption leads to the accumulation of blood components in the brain and an influx of water into the interstitial space between cells follows, causing swelling of the tissue. Cytotoxic edema is characterized by the flux of water into brain cells (predominantly brain glial cells) and is associated with trauma, ischemia and toxins.

Glial cells have compensatory mechanisms to restore water homeostasis across the cellular membrane, but following injury these mechanisms may be disrupted. TBI is characterized by mixed cytotoxic and vasogenic edema mechanisms, both contributing to overall cerebral edema. After TBI, glial cells swell [1] due to changes in the extracellular pH and concentrations of ions, including potassium, sodium, and chloride[2]. The resulting cytotoxic edema combines with the vasogenic edema caused by direct BBB injury. Reduced blood flow to the affected brain area (cerebral ischemia) leads to further ion shifts and cytotoxic edema. A vicious cycle involving components of both types of edema can proceed until the brain swells uncontrollably resulting in permanent brain damage or death. A treatment aimed at breaking the edema cycle and restoring normal ion and protein homeostasis within the extracellular space would be ideal at reversing cerebral edema and brain swelling following TBI.

SUMMARY

In alternative embodiments, the invention provides compounds, e.g., products of manufacture or devices, for reducing an edema, including e.g., a central nervous system (CNS) edema, or a spinal or a brain edema, or any tissue edema. In alternative embodiments, products of manufacture or devices of the invention comprise a concentrated protein, carbohydrate, polysaccharide or polymer solution, or osmolyte solution or rejected solute, a non-rigid hydrogel or gel, (or a combination thereof), and a semi-permeable hollow fiber membrane or a bundle or a module having a lumen, and a hollow fiber device, wherein the concentrated protein, carbohydrate, polysaccharide or polymer solution, or concentrated osmolyte solution or rejected solute, or non-rigid hydrogel or gel, passes through the lumen of the semi-permeable hollow fiber membrane, bundle or module, and the concentrated protein carbohydrate, polysaccharide or polymer, non-rigid hydrogel or gel, or concentrated osmolyte solution or rejected solute, induces an osmotic pressure that drives water into the hollow fiber device where it is removed and carried away from the edematous tissue, or from the burned, traumatized or injured tissue or area. An exemplary device of the invention is illustrated in FIG. 1, as discussed in detail, below.

In alternative embodiments, the invention provides compounds, e.g., products of manufacture or devices, for reducing an edema, e.g., a central nervous system (CNS) edema, or a spinal or a brain edema, a tissue edema, an edema secondary to an injury or a burn, the product of manufacture or device comprising:

a protein, carbohydrate, polysaccharide or a polymer solution, or an osmolyte solution or a rejected solute, or non-rigid hydrogel or gel, or a concentrated protein, carbohydrate, polysaccharide or polymer solution, wherein optionally these solutions, non-rigid hydrogels or gels are contained within a lumen or a hollow fiber of the device, wherein optionally the lumen solution or lumen contents further comprise nutrients, or drugs, and optionally the drugs and/or nutrients are for the treatment or amelioration of the edema, of a burn or injury, or an underlying disease or condition causing the edema, and optionally the drugs comprise or are small molecules or proteins, and optionally the drugs act as antibiotics, anti-inflammatories, vasoconstrictors, vascular or tissue growth stimulating agents;

a semi-permeable hollow fiber membrane or bundle/module membrane; and, a rigid or a semi-rigid hydrogel, wherein the concentrated protein, carbohydrate, polysaccharide or polymer solution, or osmolyte solution or rejected solute, or non-rigid hydrogel or gel, passes through the lumen of a semi-permeable hollow fiber membrane, and the concentrated protein, carbohydrate, polysaccharide or polymer solution, or osmolyte solution or rejected solute, or non-rigid hydrogel or gel, flowing through the semi-permeable fiber membrane, which is in contact with the tissue, induces osmotic pressure that drives water into the hollow fiber device where it is removed and carried away from the edematous, e.g., the injured or burned, tissue or area of trauma, insult or injury, wherein optionally an aqueous proteinaceous, carbohydrate or polysaccharide solution, or non-rigid hydrogel or gel, is flowed (e.g., by osmotic force) or is flowed or pumped or passively flows (such as head pressure) through the semi-permeable hollow fiber or bundle/module membrane lumen, wherein optionally the membrane completely or substantially rejects a solute but allows (relatively) easy passage of ions, electrolytes and water, and also nutrients (such as oxygen or glucose) and small molecules, proteins and other drugs, wherein optionally the hydrogel or an equivalent gel (e.g., a hydrophilic gel) can or is used to maintain a membrane-tissue contact, and optionally the edema is a central nervous system (CNS) edema, or a spinal or a brain edema, a tissue edema, an edema secondary to an injury or a burn, and optionally the temperature of the lumen solution is below about 37° C., 36° C., 35° C., 34° C. or 33° C., or below about 25° C. to 30° C., and optionally the hydrogel has a sufficient permeability to allow (relatively) easy passage of nutrients, drugs, ions, and water, and optionally the hydrogel is used to membrane-tissue contact, and optionally the hydrogel is rigid enough to maintain membrane-tissue contact and support the semi-permeable hollow fiber membrane.

In alternative embodiments, the hollow fiber device is a flexible hollow fiber device, or wherein the hollow fiber device comprises:

fibers having an outer diameter of between about 150 to 250 µm, or about 200 µm, a flexible semi-permeable hollow fiber membrane, or several semi-permeable hollow fiber membranes in a bundle or a module, wherein optionally the hollow fibers have an outer diameter of between about 100 µm to about 1 cm, and optionally the hollow fibers have an inner diameter of between about 50 to about 750 µm; or and optionally the hollow fibers comprise cellulose fibers, or regenerated cellulose fibers, or biocompatible material, or bioinert material; or and optionally the hollow fibers have a molecular weight cut-off of less than about 100 daltons for a rejected carbohydrate or a rejected salt;

and optionally the hollow fibers have a molecular weight cut-off of between about 100 to about 1000 Daltons for a carbohydrate or a polymer solution;

and optionally the hollow fibers have a molecular weight cut-off of between about 1 to about 60 kDa or greater than about 60 kDa, and optionally the hollow fibers are reverse osmosis membranes.

In alternative embodiments, the invention provides compounds, e.g., products of manufacture or devices, wherein the concentrated protein, carbohydrate, polysaccharide or polymer solution, or non-rigid hydrogel or gel, comprises:

a solute, a polymer, a carbohydrate, an osmolyte, a rejected solute, wherein optionally the solute, polymer, carbohydrate, osmolyte or rejected solute is partially or completely rejected by the semi-permeable hollow fiber membrane, wherein optionally the solute, polymer, carbohydrate, osmolyte or rejected solute is present in a concentration of between about 1% to 50% in solution, or between about 0.1% to 60% in solution, a serum albumin, or a human or bovine serum albumin (BSA), or a lumen solution of 350 g/L of a serum albumin in an artificial cerebrospinal fluid at pH 7.4.

In alternative embodiments, the hollow fiber device comprises or is a flexible hollow fiber device, optionally comprising fibers having an outer diameter of between about 150 to 250 µm, or about 200 µm. In alternative embodiments, the hollow fiber device comprises cellulose fibers, or regenerated cellulose fibers, optionally with a molecular weight cut-off of between about between about 5 to 20 kilodalton (kDa), between about 1 to 30 kDa, or about 5, 6, 7, 8, 9, 10, 11, 12, 13, 14, 15, 16, 17, 18, 19 or 20 or more kDa.

In alternative embodiments, the invention provides methods for: removing a fluid or a water from an edematous tissue, e.g., a central nervous system (CNS) tissue, or a spinal or a brain tissue, or an injured, insulted (e.g., by chemical exposure) or burned tissue, in a controlled fashion, or removing a fluid or a water from an edematous area, e.g., a central nervous system (CNS) tissue, a spinal or a brain tissue, or an injured, insulted (e.g., by chemical exposure) or burned tissue, in a controlled fashion to treat the edema, e.g., the central nervous system (CNS) edema, or a spinal or a cerebral edema; or treat or reverse a CNS, spinal or a brain inflammation or a CNS, spinal or a brain injury, or an inflammation due to an injury, a chemical exposure or a trauma, comprising:

using the product of manufacture or device of the invention, for applying or placing a concentrated protein, a carbohydrate, a polysaccharide or a polymer solution, or an osmolyte solution or a rejected solute, or a non-rigid hydrogel or a soft hydrogel or a gel, directly on and/or approximate to an injured tissue, or an exposed injured tissue, wherein the non-rigid or soft hydrogel or gel substantially conforms to the tissue site, e.g., the edematous tissue, e.g., the burned, traumatized or injured tissue area, to maximize contact area with the edematous tissue, wherein optionally an aqueous proteinaceous carbohydrate, polysaccharide or polymer solution, or an osmolyte solution or a rejected solute, or non-rigid or soft hydrogel or gel, is flowed (e.g., by osmotic force) or is pumped or passively flows (such as head pressure) across the edematous, e.g., a burned or an injured, surface area through the semi-permeable hollow fiber membrane lumen, wherein optionally a lumen solution induces an osmotic pressure driving force for water removal, wherein optionally the rate of flowing or pumping is controlled to allow fluid from the tissue to flow up to the membrane device due to osmotic pressure, wherein optionally a hydrogel or an equivalent gel (e.g., a hydrophilic gel) with significantly large permeability is used to maintain membrane-tissue contact.

In alternative embodiments, the invention provides portable or a small kits comprising a product of manufacture or device of any of the invention, optionally comprising a tubing, a hollow fiber device and an associated gel, wherein optionally the gel is a hydrogel.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 1 illustrates an exemplary product of manufacture or device of the invention in situ, in the brain of an individual; where

FIG. 3A illustrates how a dual fiberoptic probe is passed into the right cerebral cortex through a burr hole while the ICP monitor is placed contralaterally; FIG. 3B Top: graphically illustrates intracranial pressure measurements before and after the injection of distilled water; FIG. 3B Bottom: graphically illustrates NIR reflectance measurements obtained with fiberoptic probe, where an optical trigger is depicted as a vertical blue line; FIG. 3C graphically illustrates the latency between injection of water (time point 0), optical trigger, and defined threshold ICP values; as discussed in detail, below.

FIG. 9 illustrates an exemplary hollow fiber-hydrogel device of the invention; with the left image illustrating an exemplary hollow fiber attached to an inlet and an outlet port, and the right image illustrating an application of an exemplary device with multiple parallel hollow fibers embedded in a hydrogel to a brain surface; as discussed in detail, below.

FIG. 10 (FIG. 10/14) illustrates how an exemplary hollow fiber-hydrogel device of the invention improves survival in a mouse model of cytotoxic cerebral edema.

FIG. 11 graphically illustrates a percent (%) increase in brain water content, as is shown for water-intoxicated mice with no treatment (W), water-intoxicated mice treated with craniectomy only (W+C), and water-intoxicated mice treated with craniectomy+HFHD (W+C+D)

Like reference symbols in the various drawings indicate like elements.

Figures 1A, 1B:
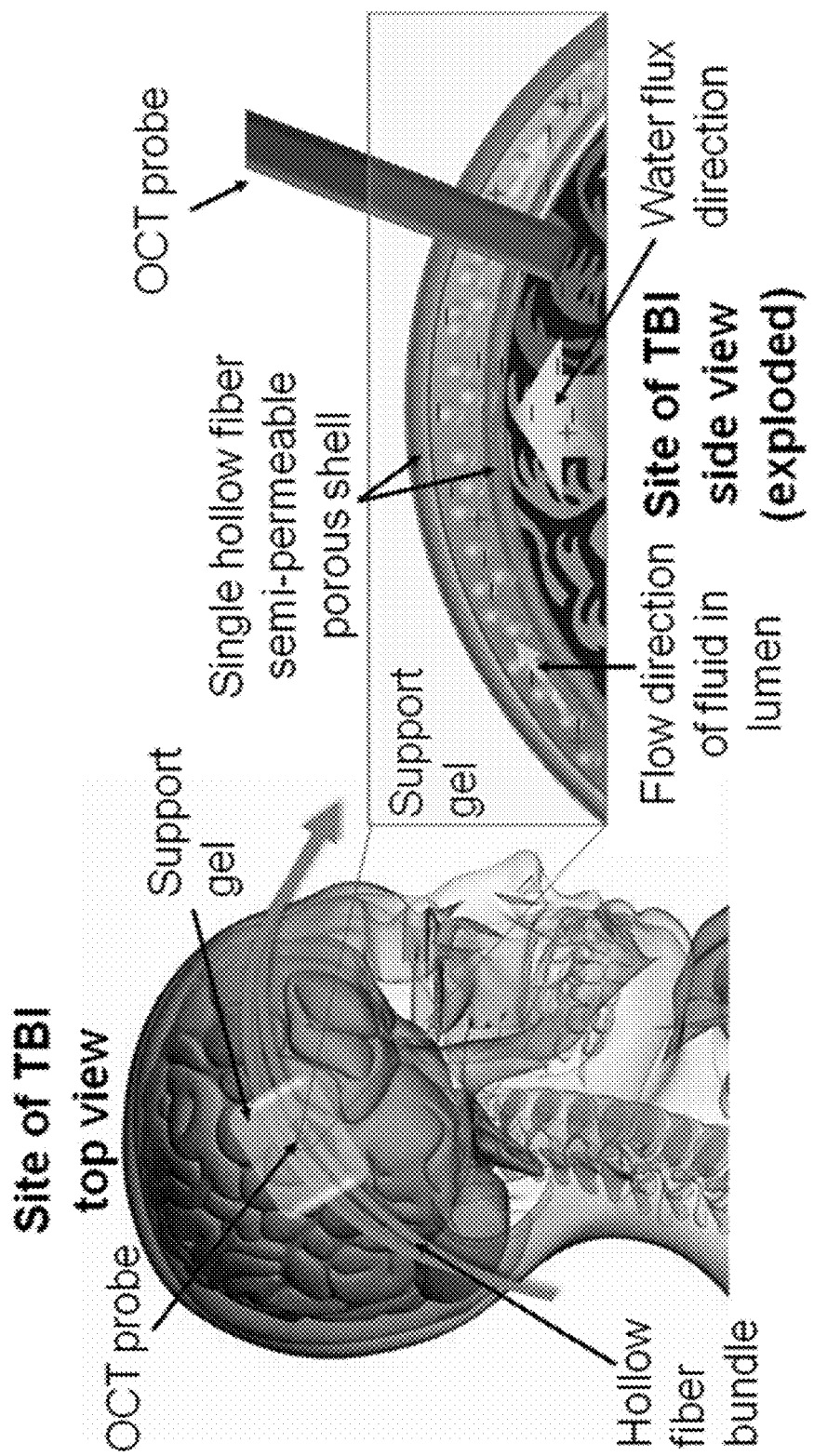
FIG. 1A illustrates a sagittal section of a patient's skull, having implanted or placed in the brain an exemplary product of manufacture or device of the invention, including an optical coherence tomography (OCT) probe, the support gel of the exemplary product of manufacture or device of the invention, and a draining hollow fiber bundle assembly; and where
FIG. 1B illustrates a close-up of FIG. 1A, illustrating the direct of water flux (efflux) (the flow direction of fluid in the CNS lumen) as effected by the exemplary product of manufacture or device of the invention; as discussed in detail, below.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

The invention provides compositions (product of manufactures, devices) and methods for the treatment and/or reversal of a CNS, a spinal or a brain edema. In one embodiment, the invention provides compositions and methods for a direct treatment and reversal of a CNS, a spinal or a brain edema, including a membrane transport device, in vitro and in vivo characterization of edema, and the sensitive early optical detection of the CNS, a spinal or a cerebral edema. The product of manufacture/device of the invention can eliminate water from edematous CNS, a spinal or brain tissue directly and in a controlled fashion.

In one embodiment, the invention provides a device using concentrated a protein, carbohydrate or polysaccharide or a polymer solution, or an osmolyte solution or a rejected solute, or a non-rigid hydrogel or a gel or any combination thereof, that pass through the lumen of a semi-permeable hollow fiber membrane or bundle/module. In one embodiment, the protein, carbohydrate, polysaccharide polymer solution, or a non-rigid hydrogel or a gel, induces osmotic pressure that drives water into the hollow fiber or bundle/module device where it is removed and carried away from the edematous site, e.g., the injured or burned area (the solution is not in direct contact with the fluid from the tissue; it is the hollow fiber membrane and/or the hydrogel that is directing contacting the tissue). In alternative embodiments, osmotic pressure is controlled by (osmotic pressure is modified by changes in): temperature, concentration, and solute. Because the osmotic pressure is generated by the presence of the rejected species in the hollow fiber or bundle/module lumen and not the ion species, the process has the advantage of maintaining ionic equilibrium. Furthermore, the system will operate in time scales on the order of the swelling rate, ensuring system stability and allowing effective feedback control. In one embodiment, scattering information from optical coherence tomography (OCT) will be used to infer swelling rate in the feedback process. The invention provides an integrated system to detect and reverse cerebral edema and, thus, reduce a CNS, a spinal or a brain damage and death in affected individuals.

The invention provides a novel membrane transport device designed to extract water from a CNS tissue, e.g., a CNS, a spinal or a brain tissue. The invention provides a novel application of a hollow fiber or bundle/module membrane transport device that can be used to actively extract water from tissue in vivo and in vitro. The invention also comprises establishing an "optical signature" of early CNS, spinal or a brain tissue edema and, subsequently, development of a feedback (closed-loop) paradigm for the device to optimally detect and treat a CNS tissue, e.g., a spinal or a brain tissue swelling in an integrated control system.

In one embodiment, the devices of the invention exploit the inevitable osmotic pressure that is generated during transport of concentrated rejected species (such as proteins or polymers) across a semi-permeable membrane in the presence of aqueous systems. Typically, membrane processes are used to separate or exchange solutes in the media in contact with the membrane. In doing so, the permeate flux is limited due to the osmotic pressure of the rejected solutes due to concentration polarization[3,4]. As an example, one of the most common models used to relate permeate flux, J, to the transmembrane pressure driving force, $\Delta P$, is the Kedem-Katchalsky model which states that [5]:

$$J = \frac{\Delta P - \sigma \Delta \pi}{\mu (R_m + R_p)} \quad (1)$$

The osmotic pressure, $\Delta \pi$, is a function of the solute concentration difference across the pores at the membrane surface. The osmotic reflection coefficient, $\sigma$, provides a measure of the membrane permselectivity, $R_m$ is the membrane resistance during ultrafiltration, $R_p$ is the extra resistance associated with any fouling, and $\mu$ is the solution viscosity. The osmotic pressure in these processes is largely regarded as a resistance to separation and must be overcome by increasing the operating transmembrane pressure. For a hollow fiber or bundle/module device, the transmembrane pressure is an average of the hydraulic pressure in the lumen minus the pressure on the outside of the fiber.

In one embodiment, the invention uses a model that takes advantage of the fundamental physics of this process by operating the process where $\Delta P < \Delta \pi$. This will result in a flux of solvent into the fiber. In addition, we will examine the controllability of the process by adjustments of $\Delta P$ or feed solution concentrations to the device. As mentioned above, this process is amenable to stable process control since the reversal process will operate on the same time scale as the swelling phenomena. In one embodiment, the invention uses an OCT probe to use as an indication of the dynamic state of tissue water infusion. FIG. 1 illustrates the overall aspects of this embodiment of the invention.

Although we will address a number of factors in determining an effective design, perhaps one of the most critical factors in developing this process is selection of solutes that will provide the appropriate driving force to this therapeutic application. In one embodiment, the invention uses protein and dextran solutions. We have done extensive research on the osmotic pressure of protein solutions and have developed the most rigorous free-solvent model for osmotic pressure prediction available [6,7]. This invention addresses the solution in terms of the protein-ion binding and hydration, and, more specifically, changes in chemical potential.

In particular, for a single protein with a monovalent salt, the free-solvent model can be described as:

$$\Delta \pi = \frac{RT}{\overline{V}_1} \ln \left\{ \frac{(N_1^{II} + (1 - v_{12} - v_{32})N_2^{II} + N_3^{II})N_1^{I}}{(N_1^{II} - v_{12}N_2^{II})N^{I}} \right\} \quad (2)$$

where $N_j^{II}$ denotes the moles of species j in the lumen, $N_1^{I}$ denotes the moles of water in the tissue, $N^{I}$ denotes the total moles of solution in the tissue, and $v_{j2}$ is the net number of moles of solution component j (1 for water, 3 for salt) that is interacting with protein (2) to make up the new solvent-interacting protein. The model has been shown to have excellent predictability of osmotic pressure for both single and binary protein solutions [8,9]. We have also successfully related this model to understanding the elusive limiting-flux phenomena in membrane separations processes and the critical flux problem using only physically relevant parameters [10, 11]. We have shown that this model has excellent agreement for uncharged polymers provided their solvent accessible surface area (SASA) can be determined [8]. In the dynamic membrane separation processes, the ion binding contribution been shown to be insignificant [10].

Figure 2:
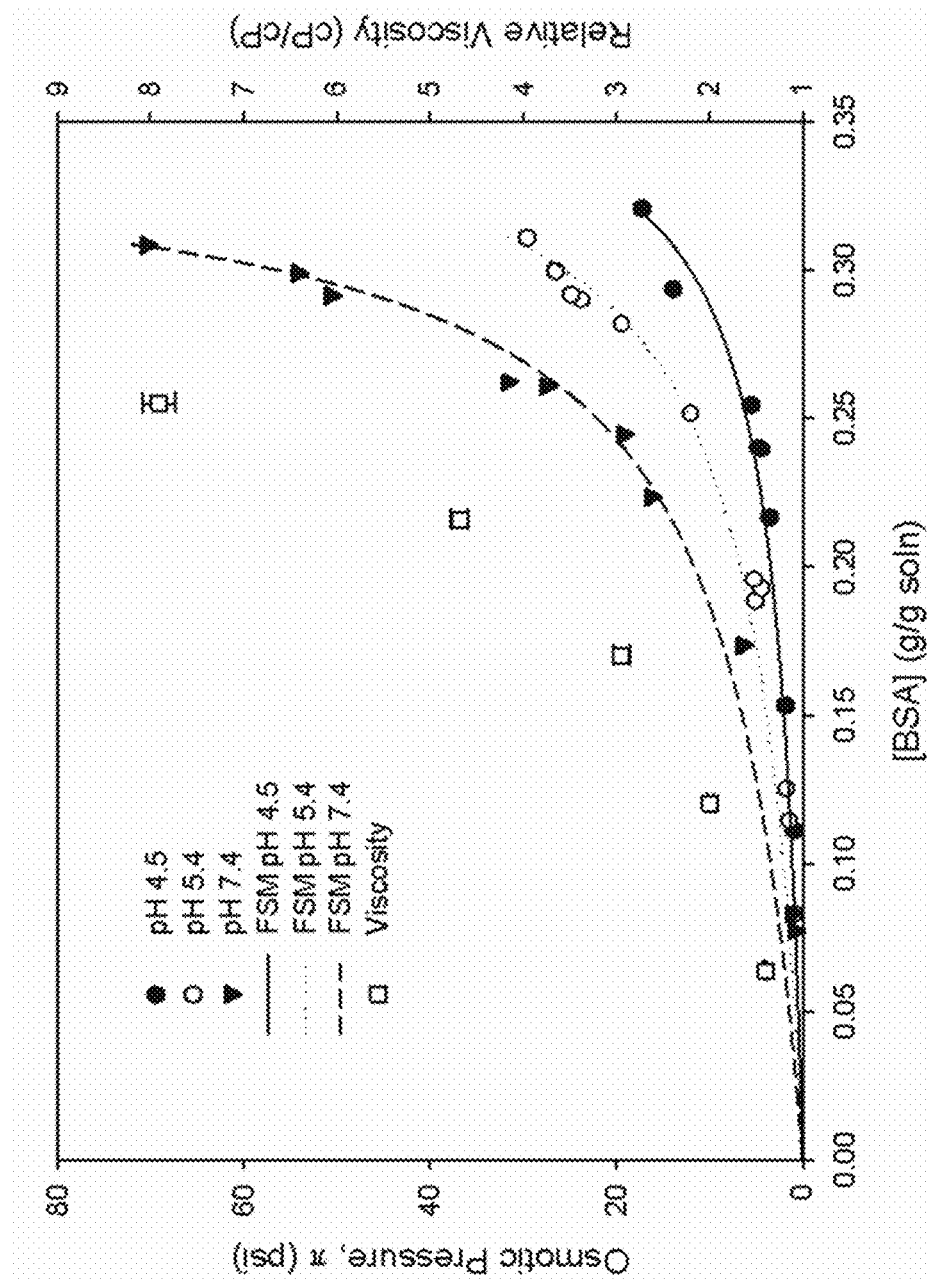
FIG. 2 graphically illustrates how many concentrated solutes and globular proteins (e.g., BSA, or bovine serum albumin) produce non-linear osmotic pressures as concentrations are varied; and how flow resistance in a fiber lumen, as measured by viscosity (relative viscosity), also increases; as discussed in detail, below.

In one embodiment, the invention incorporates this relationship to Eqn. (1) to couple solute concentration to the flux of water across the hollow fiber. As shown in FIG. 2, many concentrated solutes, and most globular proteins we studied, have the advantage of producing non-linear osmotic pressures as concentration is varied. However, flow resistance in the fiber lumen, as measured by viscosity, also increases (FIG. 2).

In one embodiment, the invention provides an integrated system to detect and reverse cerebral edema and, thus, reduce a CNS, a spinal or a brain damage and/or death in affected individuals, as illustrated e.g. in FIG. 1, which illustrates a exemplary principle of using membrane transport device for edema reversal.

In one embodiment, aqueous solutions are flowed or pumped or passively flowed (such as by head pressure) across the edematous, e.g., a burned or an injured, surface area through the semi-permeable hollow fiber or bundle/module membrane lumen. In one embodiment, the membrane is selected such that it completely rejects the solute but allows easy passage of ions, electrolytes and water, and also nutrients (such as oxygen or glucose) and small molecules, proteins and other drugs. In one embodiment, the rate of flowing or pumping or passively flowing will be controlled to allow fluid from the tissue to flow up to the membrane device due to osmotic pressure. In one embodiment, a hydrophilic gel or an equivalent gel (e.g., a hydrophilic gel) with significantly large permeability is used to maintain membrane-tissue contact. In one embodiment, the OCT probe is appropriately placed to monitor the rate of swelling. The probe signal can be sent to a feedback control system that adjusts flow or pump speed or solution concentrations to maintain appropriate tissue water and ion content.

In one embodiment, devices of the invention are capable of treating cerebral edema directly. In one embodiment, the invention provides a novel membrane transport device to eliminate water from edematous CNS, spinal or brain tissue directly and in a controlled fashion. In one embodiment, the invention provides a novel device for a clinically important syndrome.

FIG. 2 illustrates the relationship between osmotic pressure and solution viscosity for bovine serum albumin for various solution properties. This figure also shows the excellent prediction of the free-solvent model (FSM) to the data. The critical aspect of this figure relative to one embodiment of the invention is balance pumping.

In one embodiment, the invention provides for the early detection of cerebral edema with optical techniques; and provides a reliable real-time method to detect cerebral edema in vivo. In one embodiment, the invention provides a modality of detecting cerebral edema directly. Real-time optical interrogation of brain tissue with near-infrared fiberoptic probes can be capable of detecting cerebral edema [12]. In particular, we have demonstrated that reduction in NIR reflectance during early cerebral edema occurs prior to ICP elevation[12], providing a clinically-relevant time window for therapy. In one embodiment, the invention uses OCT with high temporal resolution to detect early changes in NIR light scattering during the development of cerebral edema. In one embodiment, sensitive OCT imaging of the brain cortex during the evolution of cerebral edema yields a clinically-relevant detection algorithm that can then be incorporated into a closed-loop treatment paradigm with our membrane transport device for integrated detection and direct treatment of cerebral edema (FIG. 1).

In one embodiment, the invention provides membrane transport devices designed to extract water from a CNS, a spinal or a brain tissue. In one embodiment, the invention comprises: hollow fiber or bundle/module membrane properties, solution properties, and gel properties. Design criteria can be used to determine the most appropriate choices for evaluation. Fractional factorial design analysis will be used if necessary to maximize information from each experiment and minimize the number of combinations for this work. Factorial design analysis is a systematic method of experimentally and quantitatively determining the effect of several variables on system outputs [13,14]. In one embodiment, factorial design analysis, analysis-of-variance (ANOVA) also is used to determine if parameters are statistically significant in affecting osmotic pressure and water flux [14]. In one embodiment, the appropriate manipulated variable (i.e., pump speed, solute concentration) for system control can be determined Membrane Selection. In one embodiment, hollow fibers from commercially available dialyzer constructed with various hollow fiber polymeric materials is used (e.g., Baxter dialyzers: XENIUM XPH™ (polynephron), REVACLEAR™ (polyflux), OPTIFLUX™ (polysulfone)). These systems have been selected because of their proven clinical effectiveness and appropriate molecular weight cut-off Protein/Polymer Selection, Preparation, Evaluation. In one embodiment, proteins and dextrans are used. Table 1 (below) summarizes the exemplary solutes for use in the invention. These solutes have also been selected because of their variation in size, which is coupled to their osmotic pressure. In one embodiment, free-solvent models are used to predict their range of osmotic pressure (using the solvent accessible surface area, and protein charge, as categorized by their isoelectric points, pI) [8]. Solutions properties can be selected around the physiological range of cerebrospinal fluid (in mmol/L: Na, 146.5; K, 27.7; Ca, 1.65; Mg, 1.235; Cl, 213.5, P, 0.65) [15]. In one embodiment, viscosity and density of solutions using Ostwald viscometers is determined (e.g., Cannon Fenske Cat. Nos. 75 S560, 150 N956, 200 N843) and a pycnometer (e.g., Kimble Kontes, Cat. No. 15123R-10), respectively.

TABLE 1

Properties of Selected Proteins

| Protein/Polymer | (kD) | pI | PDB | Ref. |
|---|---|---|---|---|
| Dextrans | ≥60 | | | |
| Hen egg lysozyme (HEL) | 14 | 11.0 | 1LZT | [16,, 18] |
| Bovine serum albumin (BSA) | 67 | 4.7 | — | [19] |
| Rabbit transferrin | 80 | 7.0 | 1JNF | [20,, 22] |
| Bovine lactoferrin | 80 | 9.0 | 1LFC | [23, 24] |

Figure 3:
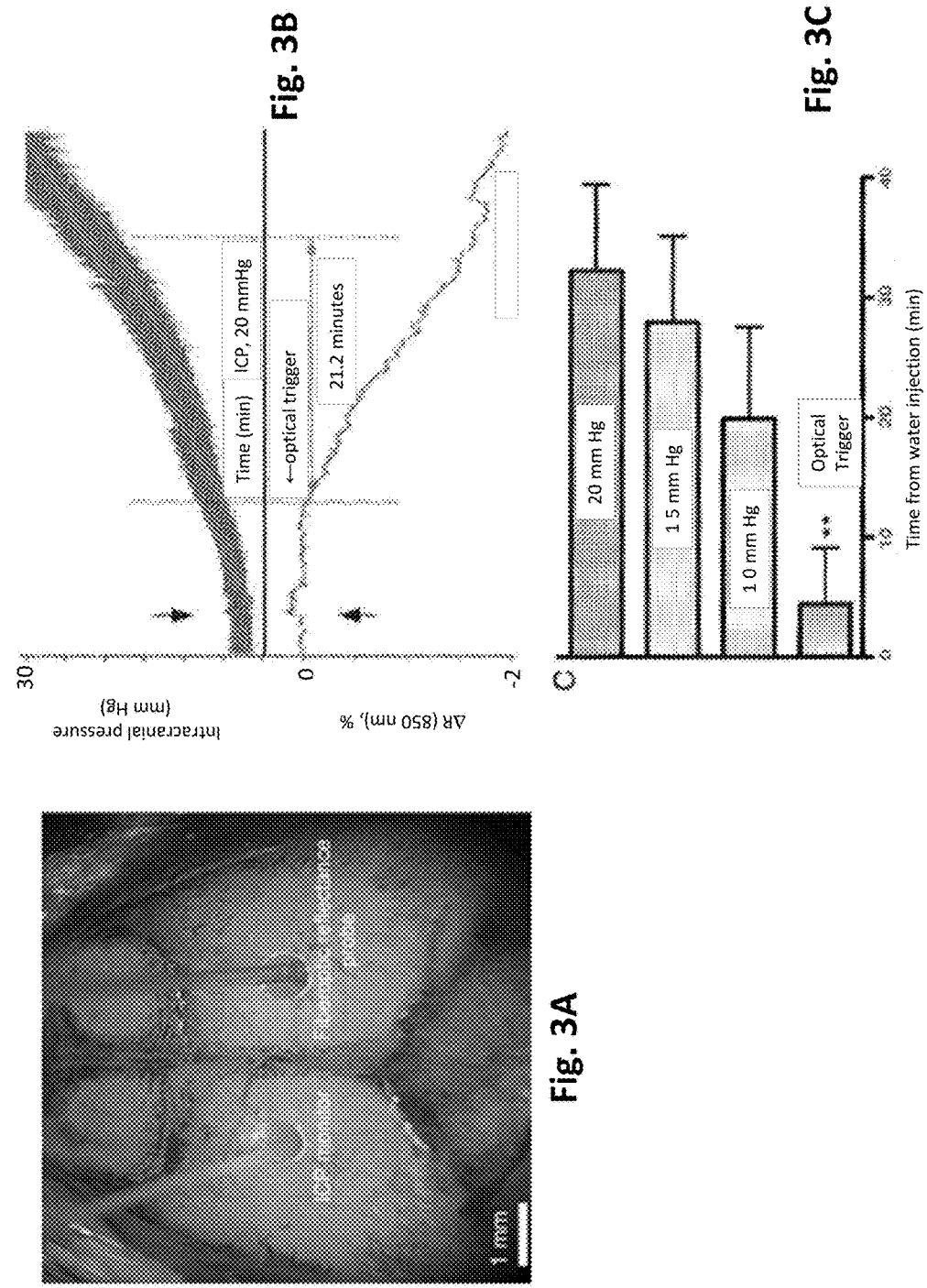
FIG. 3 illustrates the early detection of cerebral edema with a fiberoptic NIRS system using a broadband halogen light source.

FIG. 3 illustrates the early detection of cerebral edema with a fiberoptic NIRS system using a broadband halogen light source. FIG. 3 A. Dual fiberoptic probe is passed into the right cerebral cortex through a burr hole while the ICP monitor is placed contralaterally. FIG. 3 B. Top: Intracranial pressure measurements before and after the injection of distilled water (30% body weight, i.p.; black arrows). Bottom: NIR reflectance measurements obtained with fiberoptic probe. In this example, the optical trigger (vertical blue line, for significant decline in baseline reflectance) occurs 21.2 minutes prior to reaching a pathologically increased ICP of 20 mmHg FIG. 3 C. Latency between injection of water (time point 0), optical trigger, and defined threshold ICP values (n=3, mean+SEM). Optical trigger for a decline in reflectance occurs well before threshold rises in ICP to 10, 15, or 20 mmHg ** indicates p<0.02 compared to 10, 14 or 20 mm Hg.

The potential proteins listed in Table 1, are globular and, as such, their physical structures are not expected to change significantly with small changes in solution properties but can denature [25,26,27,28,29]. We will take care to avoid these solution properties of concern.

Gel Properties: in alternative embodiments, concentrations of agar (e.g., Agar, Sigma: Al296-1 kg,CAS: 9002-18-0) and NaCl for our initial gels (e.g., 0.3% agar, 3% NaCl) are used. Hydraulic permeability will be determined or checked.

In one embodiment, the device of the invention can actively remove water from a CNS, a spinal or a brain tissue in vivo, which can be demonstrated in animal models of cerebral edema.

Models of cerebral edema that can be used: water intoxication and cortical freeze injury [12,30]. The water intoxication model is a model of pure cytotoxic edema involving intraperitoneal injection of distilled water (30% body weight). This leads to a reproducible pattern of progressive cytotoxic edema and increased ICP (FIG. 3). We will apply the membrane transport device on the surface of the mouse brain after exposure via atraumatic craniectomy. This will allow adequate contact of the gel/fiber matrix to the brain surface for water efflux. Endpoints will include brain water content, measured as described [12] by a sensitive wet-dry weight method, and neurological outcome by direct observation. The cortical freeze injury model is a model of pure vasogenic edema. Cortical freeze injury disrupts the BBB and leads to water influx from the bloodstream. Following cortical freeze injury, we will immediately apply the membrane transport device to the surface of the brain. Endpoints as before will include brain tissue water content and neurological outcome.

In one embodiment, the devices of the invention provide excellent surface contact between a CNS, e.g., a spinal or a brain surface, and the membrane transport device. In one embodiment, the appropriate gel concentrations are used to conform to the CNS surface or tissue, e.g., spine or brain. In one embodiment, water efflux from the CNS, spine or brain occur through the dura (membrane covering the brain), and water can flow across the mouse dura in response to osmotic gradients [31]. The water intoxication and cortical freeze injury models can show a significant increase in brain tissue water content in order to demonstrate that membrane transport devices of the invention can reverse this. We have demonstrated significant increases in brain water content using these models in previous work [12,30].

The ability of optical coherence tomography (OCT) imaging to detect cerebral edema can be tested. Previously reported results demonstrate a reduction in NIR reflectance preceding ICP elevation during early cerebral edema using a dual fiber optic reflectance detector weighted toward measurement of scattering through a close separation between fiber cores [12]. The ability of OCT to detect these same changes with improved spatiotemporal resolution can be tested. OCT can be thought of as an optical analog of ultrasound imaging, in which the intensity and time delay of reflected light is used to generate cross-sectional images of tissue microstructure with micron-level resolution[32]. Second-generation instruments utilize Fourier-domain, rather than time-domain, detection to realize several orders of magnitude in system sensitivity that can be used to increase acquisition speed and stability [33,34,35,36,37]. Multi-functional versions of such systems can be implemented using the unrestricted use of fiber-optic components [38], and can be adapted for endoscopic application[39,40]. In addition, it has been demonstrated that optical scattering and reflectivity coefficients can be extracted from OCT images accurately and with more than sufficient spatiotemporal resolution [41,42]. The subsurface structure of the animal models can be endoscopically probed, as described herein to determine the value of various optical parameters from optical coherence tomography (OCT) images. A similar reduction in tissue reflectivity with the onset of cerebral edema, and an increase with the use of a membrane transport device of this invention. These measurements can be used for inferential prediction of tissue swelling and apply this to a feedback control strategy.

To separate the effects of the reduction in NIR reflectance inherent to the sample from changes in intensity caused by the system, two methods are employed. The first is the introduction of a small reference reflector of known reflectance within the field of view of the probe but above the tissue sample surface. This will allow normalization of the backscattered intensity from within the tissue to yield directly comparable depth-resolved maps of absolute tissue reflectivity, even between different imaging sessions. Second, our analysis takes advantage of the fact that we obtain depth-resolved information to extract optical parameters based on depth-dependent changes in reflectivity. In basic principle, we expect to see a roughly exponential reduction in the rate of drop-off in the reflectivity profile of light intensity as a function of depth below the tissue surface with the onset of cerebral edema and a reversal with the application of the membrane device. The relatively high degree of optical scatter typically found in neural tissue now becomes advantageous, as it should be easier to observe changes in a high depth-dependent rate of change in back-reflected intensity.

FIG. 4A graphically illustrates data acquired from optical coherence tomography (OCT) imaging of excised murine brain tissue. A small section was cut and laid flat, with a buffer solution applied topically at regular intervals to half the tissue. An image composed of 2048 depth profiles (2 mm depth) spanning 5 mm in width was acquired over the boundary between the two halves (indicated by arrow). Signal to noise (SNR) profiles of backreflected intensity as a function of depth beneath the tissue surface were determined for each half Two effects should be noted in the resulting plots. First, there is a significant difference in absolute backreflected signal level at all depths between the two halves as a result of the uncalibrated difference in their water content. Second, there is a visible difference in the slopes of these intensity profiles that are indicative of differences in scattering coefficients.

Reduction in Near-infrared (NIR) Light Reflectance During Cerebral Edema

Our previous results show that there is a reduction in NIR optical reflectance during the early development of cerebral edema (FIG. 3) [12]. These results, obtained in the water intoxication model of cytotoxic edema, provide proof of principle for the early detection of CNS, spinal or a cerebral (e.g., brain) edema with optical methodologies.

Efficacy of Exemplary Membrane Transport Device of the Invention in Removing Water We performed two initial experiments. First, we place a commercially available hollow fiber cartridge (Baxter CF15 Dialyzer) 25 cm above a container of water (that was in contact with the fiber bundle shell) and pumped a solution (Sigma Cat. No. A3059-100G, 60 g/L BSA solution, 40 mM KCl, pH 6.9) at 8 mL/min through the lumen of the bundle fibers. We ran the system for 2 h and removed 61.5±4.95 mL from the container via the osmotic pressure gradient. Next, we removed the hollow fibers from a similar bundle and placed onto a 0.8% agar gel which was partially submerged in a KCl solution (40 mM KCl). We pumped a solution of (100 g/L BSA solution, 40 mM KCl, pH 7.1) through the lumen of the bundles for approximately 3 h at a flowrate of 8 mL/min. The contact area was approximately 243 mm$^2$. The results showed that 60% of the KCl solution was removed by osmotic pressure by the fibers via the gel. We also performed a control study using a similar gel (area of 206 mm$^2$) partially submerged in a KCl solution. For the control only 7.6% of the KCl solution was removed through evaporation.

Figure 5:
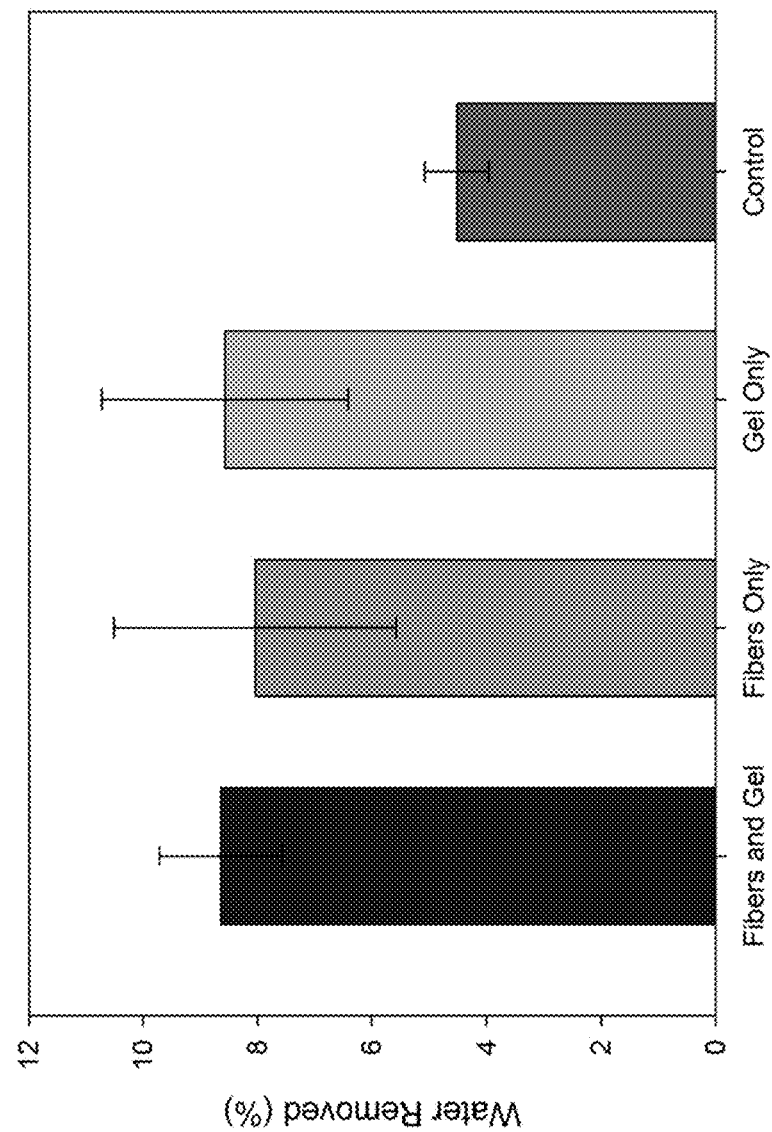
FIG. 5 graphically illustrates the amount of water removed (%) by a brain by each condition (see below) after 30 minutes of contact with an exemplary product of manufacture of the invention, the first column indicating fibers and gels, the second column indicating fibers only, the third column indicating gel only, and the fourth column (the right) the negative control; as discussed in detail, below.

Efficacy of Prototype Membrane Transport Device in Removing Water from Brain Tissue FIG. 5 graphically illustrates the amount of water removed (%) by each brain by each condition after 30 minutes of contact with an exemplary product of manufacture of the invention, the first column indicating fibers and gels, the second column indicating fibers only, the third column indicating gel only, and the fourth column (the right) the negative control. Contact areas for non-control cases was held constant. Two brain halves were studied using each condition (n=2). Flowrate: 8 mL/min.

In preliminary studies with postmortem dissected brain tissue, we have applied the membrane transport device and verified removal of water from the brain tissue. The dissected brains were cut into half for use in one of the three conditions or as a control. The three conditions tested were: 1) fibers were placed on top of an agar gel which was in direct contact with the cerebral cortex (fiber and gel); 2) fibers were placed directly onto the cerebral cortex (fibers only), and; 3) gel was placed directly onto the cerebral cortex (gel only). In all studies, the fibers had a BSA solution (100 g/L BSA solution, 3% NaCl solution, pH 7.22) passed through them, with a flowrate of 8 mL/min, to induce a flux of water from the tissue. The gel was prepared using 0.3% agar and 3% NaCl solution. The gel thickness was ~5 mm. The contact area for all studies was 100 mm$^2$. Initially, we immersed the tissue in distilled water for 40 min to allow maximum uptake of water (~13%). After the tissue had absorbed water, each of the them was studied using one of the three conditions or the control. In all studies, the brains were wrapped in polyvinylidene chloride film to minimize evaporation and allowed 30 min for water removal. The tissue was weighed before and after each experiment to determine the amount of water removed. The results (FIG. 5) show that all of the three conditions removed a significant amount of water. From the combined observations, it is likely that further time given to the experiment would result in larger fluid removal using the combined hollow fiber/gel system.

Second-generation Optical Systems

Two second-generation optical systems can be utilized. The first is a higher resolution system in the near-infrared integrated into an upright microscope. The second has been designed for wider field imaging of structures that cannot be imaged with the upright microscope system, and will utilize a source in the 1300 nm wavelength range and has been adapted for use with a variety of imaging probes.

One high resolution system has been optimally tuned for the following objectives: UPlan S-Apo 20× (0.75 NA, 0.65 WD) for detailed high-resolution images and the UPlan S-Apo 4× (0.16 NA, 13.0 WD) for slightly lower resolution, wider-field of view images.

Figure 6:
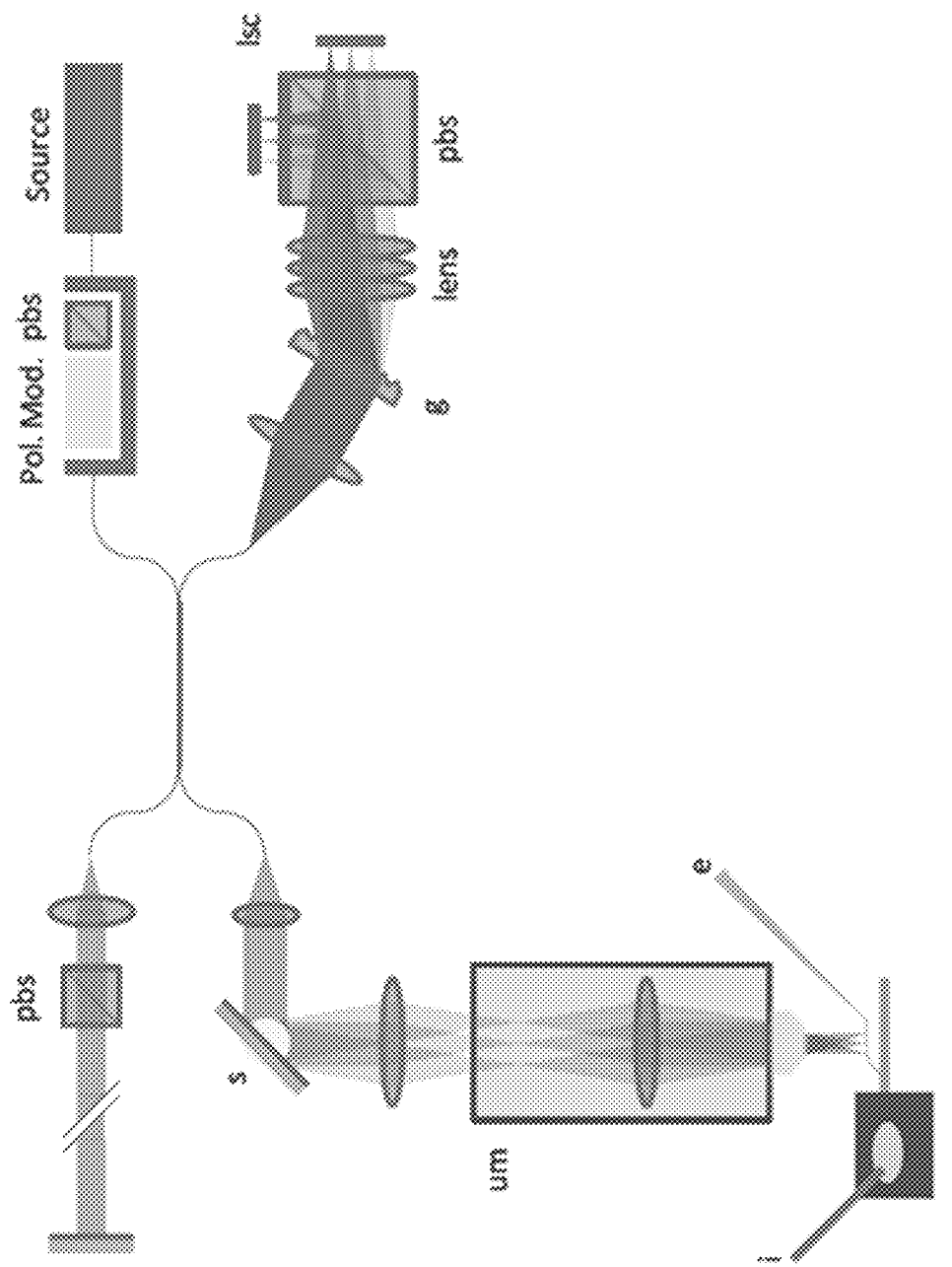
FIG. 6 illustrates a diagram of a high-resolution spectral-domain optical coherence tomography system integrated into a fixed stage upright microscope; as discussed in detail, below.

FIG. 6 is a diagram of a high-resolution spectral-domain optical coherence tomography system integrated into a fixed stage upright microscope (pbs: polarizing beam splitter, Pol. Mod.: polarization modulator, g: diffraction grating, lsc: line scan camera, s: scanning galvanometers, um: upright microscope, e: recording electrode, i: illumination source). A schematic of the SD-OCT system is shown in FIG. 6: Light generated by a broadband source Ti:Sapphire laser (INTEGRAL OCT™, FemtoLaser Inc.) is split by a fiber-based 70/30 splitter. The source emits an average power of 80 mW centered at 820 nm and a full-width-at-half-maximum spectral bandwidth of ~160 nm, resulting in an axial resolution of ~1-2 µm in air. Light reflected from the sample arm of the interferometer is combined with that reflected from the static reference arm and directed into the detection arm. This consists of a high-resolution polarization-sensitive spectrometer in which the light is collimated, dispersed by a high efficiency (>90%) transmission grating (1200 lines/mm), focused and split via a lens and polarizing beam splitter cube onto two synchronized line scan cameras. The line scan cameras (Basler Sprint series) can acquire 140 k depth profiles per second. This system is capable of shot-noise limited detection and an effective spectral resolution of 0.14 nm, resulting in a ranging depth of ~2 mm in air. The sample arm beam path of the SD-OCT system has been integrated into an Olympus BX61WI™ upright microscope adapted for electrophysiology (FIG. 13). The microscope itself is capable of motorized axial stepping with a resolution of 10 nm, and is fitted with a Sutter Instruments MT78 motorized platform stage for lateral stepping. The video port has been used to introduce the SD-OCT beam into the microscope. An optical fiber port collimator sends light to a galvanometer-based scanner set (Cambridge Instruments XY-set customized with no differential controller for lower stationary position jitter). The pivot points of the scanner will be relayed to the back focal plane of the microscope objective to minimize field curvature. This system has been optimally tuned for the following objectives: UPlan S-Apo 20× (0.75 NA, 0.65 WD) for detailed high-resolution images and the UPlan S-Apo 4× (0.16 NA, 13.0 WD) for slightly lower resolution, wider-field of view images.

The sample arm beam path of the SD-OCT system has been integrated into an Olympus BX61WI™ upright microscope adapted for electrophysiology. The microscope itself is capable of motorized axial stepping with a resolution of 10 nm, and is fitted with a Sutter Instruments MT78 motorized platform stage for lateral stepping. The video port has been used to introduce the SD-OCT beam into the microscope. An optical fiber port collimator sends light to a galvanometer-based scanner set (Cambridge Instruments XY-set customized with no differential controller for lower stationary position jitter). The pivot points of the scanner will be relayed to the back focal plane of the microscope objective to minimize field curvature.

Figure 7:
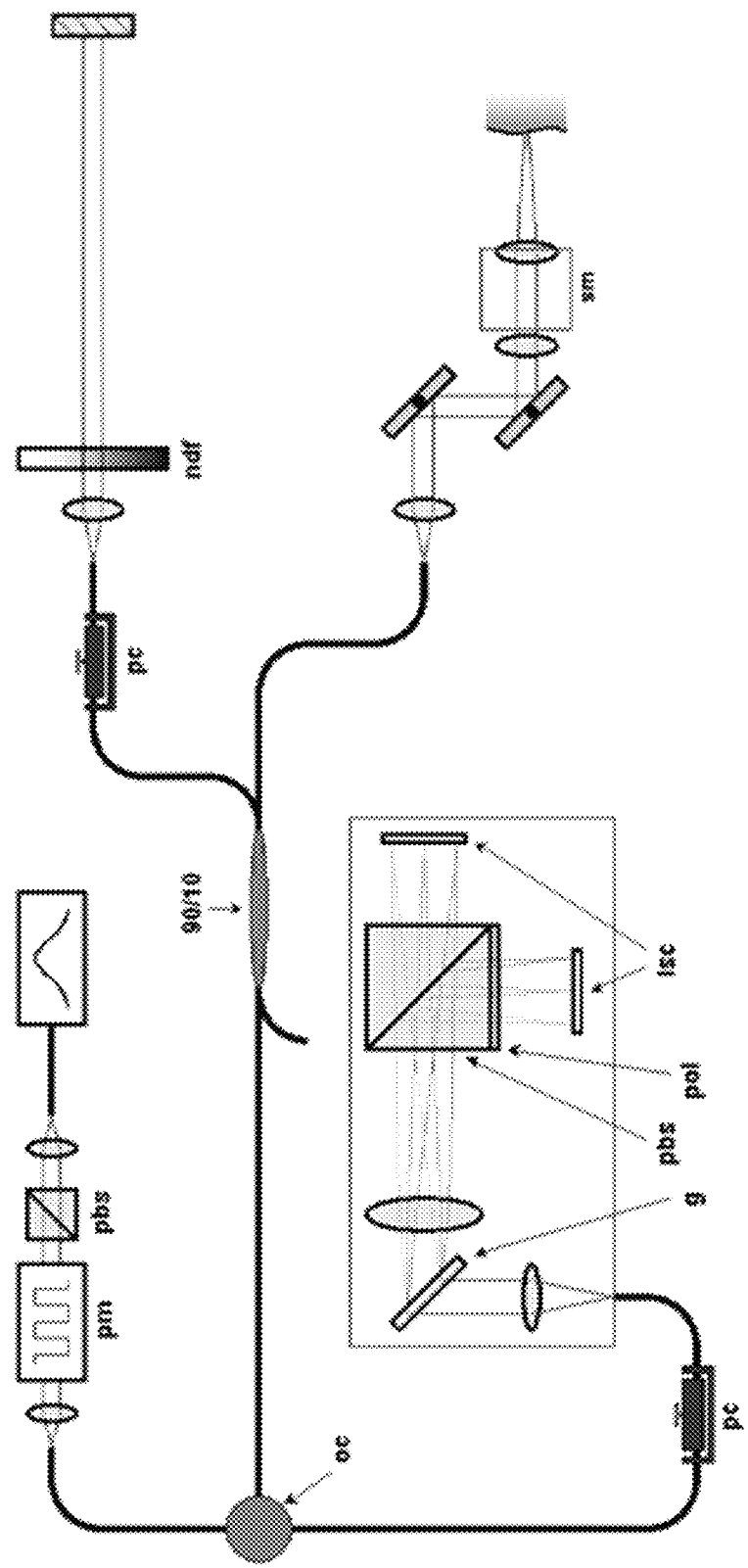
FIG. 7 illustrates a schematic of a wide field imaging system; as discussed in detail, below.

A schematic of the wide field imaging system is shown in FIG. 7. The output of a custom-built fiber-coupled source powered by 8 SLEDs with an overall power of 68 mW and a FWHM bandwidth of 213 nm centered in the 1300 nm range is aligned with a polarizing beam splitter and an electro-optic polarization modulator such that transmitted light can be toggled between polarization states that are perpendicular in a Poincaré sphere representation. This light is sent into an interferometer composed of a fiber circulator and a 90/10 fiber splitter for efficient sample arm illumination and collection. The reference arm is composed of a lens, polarizer, variable neutral density filter, and a stationary mirror. Light returning from both arms passed back through the fiber splitter and circulator and was directed to a polarization-sensitive spectrometer. In the spectrometer, the optical spectrum was dispersed by a transmission grating, focused with a planoconvex lens, and split with a polarizing beam splitter cube onto two Goodrich line scan cameras (SU1024LDH, 1024 pixel InGaAs 14-bit CAMERA-LINK™ A=$\pi r^2$ output at 45 kHz). A polarizer is introduced between the polarizing cube and one camera to improve rejection of horizontally polarized light from the vertical polarization channel.

Other Applications for Use of Exemplary Edema Reduction Devices of the Invention In alternative embodiments, devices of the invention are portable, and advantages of this portable design, or "portability", is its use in the event of a catastrophic event or in the warfare theatre during active combat.

In alternative embodiments, the design for flow-through the lumen (the protein solution) can be achieved with very low flow including gravity feed. In alternative embodiments, a CerebroSpinal Fluid (CSF) solution can be stored in flexible bags (just as lactated ringer's solution or saline solutions used in hospitals and temporary combat emergency facilities such as MASH (Mobile Army Surgical Hospital).

In alternative embodiments, these bags are connected to transfer tubing and the device and hung over the patient's injury, the resulting flow will be sufficient to induce the osmotic pressure effect. In the field, the device design will be effective for first responders, and can be carried in a small kit that supplies the tubing, hollow fiber device and the associated gel. The kit can be rapidly deployed and the flexibility of the fibers, as well as the efficacy of the device (it does not need to cover the entire edematous, e.g., burned or injured area), allows for its use in a number of emergency applications were skull fracture, skull removal or craniotomies have taken place or for use with reducing swelling in other areas of the body were contact with the device is assessable such as spinal swelling.

Figure 8:
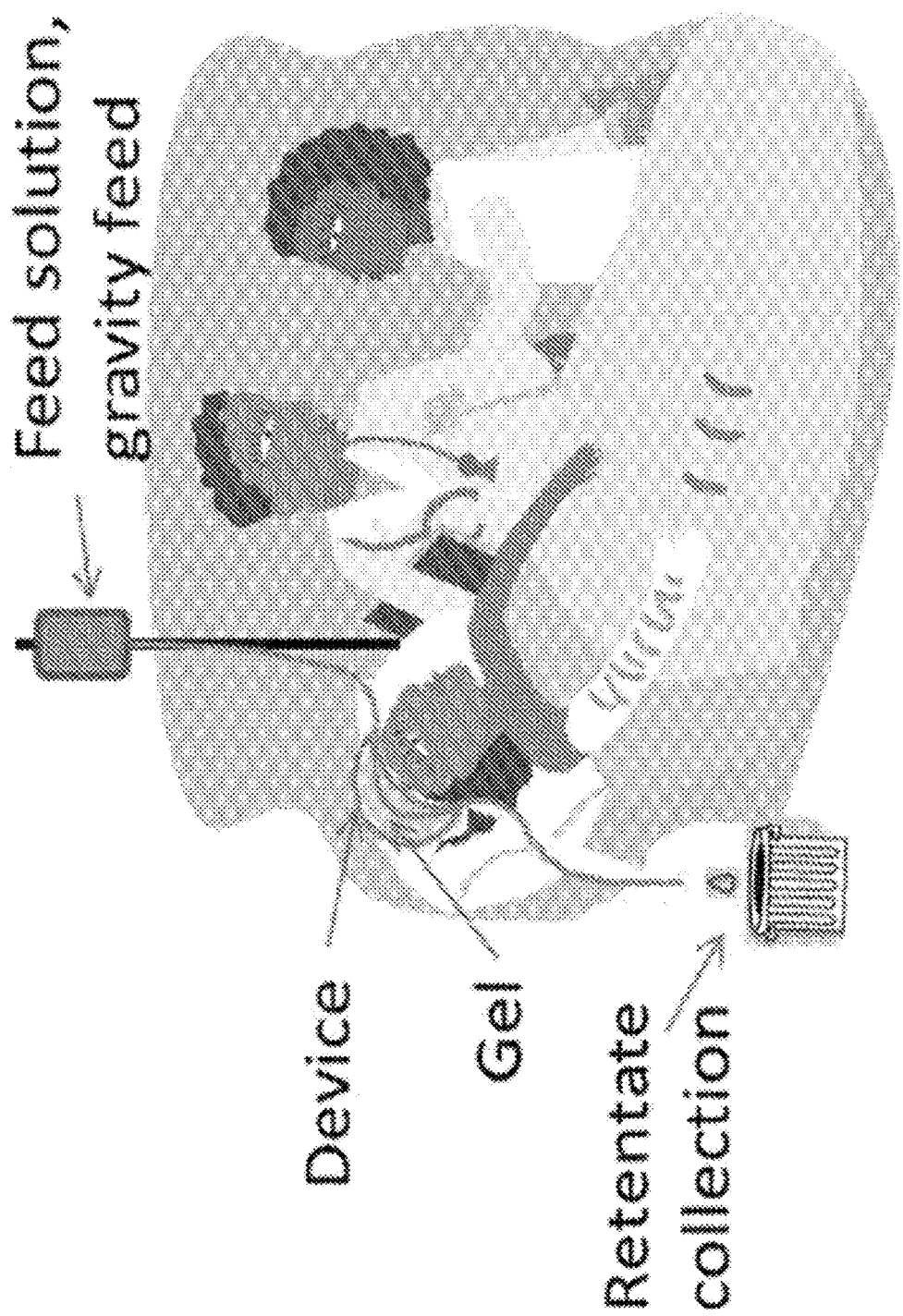
FIG. 8 illustrates a schematic of an exemplary, optionally portable, device of the invention, and this exemplary application for a device, e.g., a portable device, of the invention; as discussed in detail, below.

FIG. 8 is a schematic of an exemplary, optionally portable, device of the invention, and this exemplary application for a device, e.g., a portable device, of the invention. The gravity feed of the solution is an alternative embodiment, as is the retentate collection device illustrated.

Kits and Instructions

The invention provides kits comprising compositions and methods of the invention, including instructions for use thereof In alternative embodiments, the invention provides kits comprising a composition, product of manufacture, or mixture or culture of cells of the invention; wherein optionally the kit further comprises instructions for practicing a method of the invention.

In alternative embodiments, the invention provides portable, movable and/or small kits that can comprise tubing, a hollow fiber device and the associated gel.

The invention will be further described with reference to the following examples; however, it is to be understood that the invention is not limited to such examples.

EXAMPLES

Example 1: Hollow Fiber-hydrogel Devices of the Invention Improve Survival Following Cerebral Edema The data presented herein demonstrates that embodiments of hollow fiber-hydrogel devices of the invention effectively improve survival following cerebral edema. In alternative embodiments of the invention provides hollow fiber-hydrogel devices (HFHD) for direct surface contact-based treatment of severe cerebral edema. In alternative embodiments the invention provides direct surface-contact-based treatments using an exemplary hollow fiber-hydrogel devices (HFHD) of the invention. Using devices of the invention, tissue water extraction and survival is successfully enhanced in mice with severe cerebral edema.

Summary

Methods:

Brain edema was induced in adult mice via water intoxication by intraperitoneal water administration (30% body weight, i.p.). Control mice received no treatment. A distinct group of mice were treated with craniectomy but no device application. A third experimental group was treated with craniectomy and the exemplary HFHD of the invention. This exemplary HFHD contained a lumen solution of 350 g/L BSA in artificial cerebrospinal fluid at pH 7.4 and room temperature. Brain water content and survival were assessed as endpoints.

Results:

Craniectomy and application of the HFHD enhanced survival in mice with severe cerebral edema. Mice treated with a craniectomy and HFHD (n=5) survived up to five 30 hours longer than mice treated with craniectomy only (n=5) (p<0.0001) or no treatment (n=5) (p<0.0001). Mice treated with a craniectomy and HFHD (n=5) had a survival rate of 80% within the observation period (360 minutes), whereas no mice treated with craniectomy only (n=5) or no treatment (n=5) survived longer than 53 and 35 minutes, respectively. Statistical significance was observed for survival rate between the animals treated with HFHD (n=5) vs. craniectomy only (n=5) (p<0.0001), and HFHD vs. no treatment (n=5) (p<0.0001).

Conclusions:

Here we demonstrate the feasibility of an exemplary HFHD of the invention to treat a cerebral edema using this art-accepted animal model. Advantages of this exemplary HFHD of the invention includes modifiability in terms of rate of water removal based on alterations in lumen solution properties; and modifiability in terms of size and contact area to the brain surface. These results indicate that controlled water extraction from edematous brain tissue can be performed and lead to increased survival compared to craniectomy only. In alternative embodiments, exemplary HFHD of the invention is used to treat traumatic CNS, spinal or brain injuries.

Methods

Hollow Fiber-hydrogel Devices

The exemplary hollow fiber-hydrogel device (FIG. 1) (hereafter HFHD) comprises or consists of a hollow fiber semi-permeable membrane system embedded in a moldable, soft hydrogel that is placed directly on the exposed edematous, e.g., burned or injured, tissue and will conform to the edematous, e.g., burned or injured, area to maximize contact area. In addition, the hydrogel will ensure that the contact between fiber and tissue is maintained. An aqueous fluid containing concentrated, fully rejected species (such as proteins) is passed through the lumen of the fibers. The hydrogel contact is continuous through the moldable gel and the tissue resulting in an inevitable osmotic pressure. This pressure gradient will gently remove fluid from the tissue through the gel and ultimately through the fibers and away from the subject.

In one embodiment, a major advantage of using the HFHD lies in its intrinsic nature. The water removal rate can be controlled and modified as treatment requires based on alterations in the lumen solutions properties. A few of the possibilities are changes in the impermeable solute concentration to alter the osmotic pressure of the lumen solution, altering the flow properties (e.g. flow rate or viscosity), and increasing the number of hollow fibers or treatment contact area.

In alternative embodiments, the choice of hollow fibers requires flexibility and knowledge of the lumen solution properties. The smaller the hollow fiber outer diameter is, as well as the hollow fiber material, will determine the flexibility and, more importantly, the range of surface area which can be treated. Flexible hollow fibers with a relatively small outer diameter (200 µm) will be able to mold to brain gyrations while the hydrogel ensures that fiber-tissue contact is maintained.

In this study, the exemplary HFHD was developed using regenerated cellulose fibers with a molecular weight cut-off of 13 kDa (Spectrum Laboratories, Inc. 132294). The contact area between the hollow fibers and the cerebral cortex was 17.8±2.2 mm$^2$. The solution passing through the hollow fibers (lumen solution) operated at a flowrate with a Reynolds number (Re) between 50 and 100.

Treatment with the exemplary HFHD consisted of the fibers being placed directly onto the mouse cerebral cortex following craniectomy, with a hydrogel covering the fibers and the exposed tissue (FIG. 2). The hydrogel was created by dissolving agar into the same solution properties as the lumen solution without the impermeable solute (0.3% agar, artificial CSF, pH 7.4 gel).

Lumen Solution

The lumen solution consisted of concentrated bovine serum albumin (BSA) (impermeable solute) in a saline solution at pH 7.4. BSA was used because the osmotic pressure of concentrated BSA solutions has been extensively studied for various solution properties[15,16] and because it is completely rejected by the hollow fiber membrane. The BSA solution was made by dissolving BSA (Research Products International Corp. A30075) into the saline solution. The BSA was mixed using a stir-plate at room temperature and the pH was adjusted using 1 M NaOH or 1 M HCl. In these experiments, a BSA concentration of 350 g/L in a CSF at pH 7.4 was used. This BSA concentration has an osmotic pressure of approximately 28 psi.[15]

The saline solution used in this study was isotonic saline mimicking the CSF (artificial CSF, a CSF). A CSF was prepared by dissolving the salts in nanopure (ddH$_2$O) water following the protocol described for a CSF.[4]

Animals: all experiments were conducted under protocols (A-20100018) approved by the University of California, Riverside Institutional Animal Care and Use Committee (IACUC). Adult female ten- to twelve-week-old mice were used in all experiments.

Surgical technique: Prior to induction of water intoxication, animals were anesthetized with an 80 mg/kg ketamine, 10 mg/kg xylazine mixture. Surgical procedures began only after determining that an adequate plane of anesthesia had been reached with the loss of paw pinch reflex. Reflex activity was continuously monitored throughout the procedure and supplemental doses of half of the initial dose were provided as needed.

After anesthesia, the animals were placed into a standard rodent stereotatic frame. A midline skin incision was made and reflected. A right-sided craniectomy was performed (anterior border: coronal suture, posterior border: lambdoid suture, medial border: midline, lateral border: temporalis attachment). The dura was carefully and atraumatically opened with microdissection.

Water Intoxication Model

Cytotoxic cerebral edema from water intoxication was produced as previously described.[5] Mice were injected with distilled water (30% body weight, i.p.). Approximately five minutes post-injury, treatment began. The three experimental groups were: (1) no treatment (water intoxication only); (2) craniectomy-only; and (3) craniectomy+HFHD.

Endpoints included survival time and brain water content analysis. Survival was assessed over the course of 360 minutes following water intoxication in all mice. After the treatment procedure, brains were dissected out post-mortem and subjected to wet-dry weight comparisons to determine % water content as previously described.[5,17]

Histology

In order to determine the tissue damage caused by treatment using the exemplary HFHD, three animals were used. For these animals, the surgical procedure was completed but water intoxication was not induced. The HFHD was applied directly to the brain tissue for three hours. The animals were then euthanized. The brain tissue was then dissected and frozen for post-mortem histology. 50 μm coronal cryostat sections were prepared, stained with Data Analysis Intergroup comparisons of survival times and brain tissue water content were done using one-way ANOVAs and post-hoc Bonferroni tests.

Results

Improved Survival Following Treatment with the Exemplary Hollow Fiber-Hydrogel Device of the Invention:

Mean survival times following water intoxication were determined for untreated, craniectomy-only treated, and craniectomy+HFHD-treated mice (FIG. 3A). Survival time for the no treatment group was 31±3.1 minutes (n=5). Treatment with craniectomy only slightly increased survival time to 48±4 minutes (n=5). Treatment with craniectomy+HFHD markedly improved survival time to 333±28 minutes (n=5). Four of five (80%) of the HFHD-treated mice actually survived throughout the entire 360-minute observation period (and then were sacrificed to obtain brain water content data). Thus, mice treated with a craniectomy+HFHD survived approximately five hours longer, before termination, than mice receiving no treatment or craniectomy only (FIG. 3B). Significant differences in survival were observed statistically between the craniectomy+HFHD vs. craniectomy only group (p<0.0001); and significant difference in survival was observed between the craniectomy+HFHD vs. no treatment group (p<0.0001).

Figure 4:
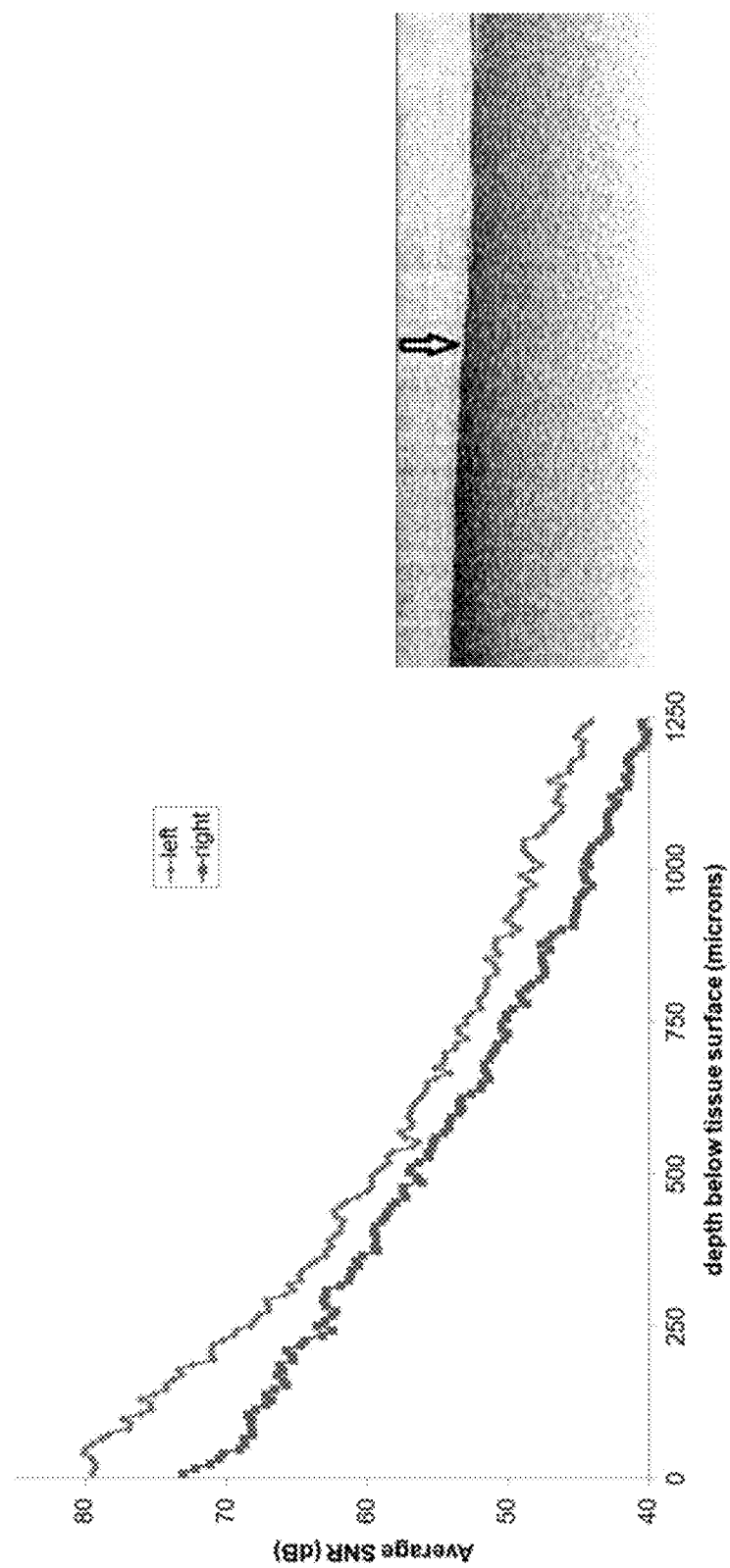
FIG. 4A graphically illustrates data acquired from optical coherence tomography (OCT) imaging of excised murine brain tissue, where (as illustrated in FIG. 4B) an image composed of 2048 depth profiles (2 mm depth) spanning 5 mm in width was acquired over the boundary between the two halves (indicated by arrow); as discussed in detail, below.

Brain water content: In addition to enhancing survival, the HFHD was able to remove a significant amount of water from brain tissue. Using wet-dry brain weights, % brain water content was determined for control non-water intoxicated mice (n=5), untreated water-intoxicated mice (n=5), water-intoxicated mice treated with craniectomy only (n=4), and water-intoxicated mice treated with craniectomy+HFHD (n=5) (FIG. 4). No significant differences were found between the water content of the left and right hemispheres for any treatment group, so the water content of both hemispheres is shown. Of course, based on survival differences, there was a different time of sacrifice for brain water content analysis. The untreated non-water intoxicated control mice were sacrificed; untreated water-intoxicated mice all expired within 35 minutes following injection; water-intoxicated mice treated with craniectomy only all expired within 53 minutes following injection; and 80% of the water intoxicated mice treated with craniectomy+HFHD were sacrificed at the end of the observation period.

The brain water content for the untreated water-intoxicated animals (W), water-intoxicated animals treated with a craniectomy only (W+C), and water-intoxicated animals treated with a craniectomy and the HFHD (W+C+D) was higher, in all cases, than the brain water content for the untreated control animals. Brain water content of untreated control mice without water intoxication was 64.2±1.4%. The percent increase of the brain water content of untreated mice with water intoxication was 5.4±5.8%, which was significantly elevated compared to non-water intoxicated animals (p<0.05). Mice treated with water intoxication and craniectomy only had a percent increase in brain water content of 10.3±3.1%, which was significantly higher than both the untreated water-intoxicated mice (p<0.05) and the untreated non-water intoxicated mice (p<0.0001). However, water-intoxicated mice treated with a craniectomy+HFHD had a percent increase in brain water content of 4.3±2.3% which is significantly lower than the craniectomy only group (p<0.01). Indeed, water-intoxicated mice treated with craniectomy+HFHD have brain water content similar to non-water intoxicated untreated mice (no statistical significance is observed, p>0.05).

Tissue damage caused by HFHD treatment: To further validate the use of an exemplary HFHD of the invention to treat water intoxication and general edema, histology staining of the brain for non-water intoxicated mice treated with a craniectomy and the HFHD was performed. Histology was performed to determine the extent of tissue damage caused by the HFHD treatment protocol, which included the craniectomy, HFHD placement, and water removal via the HFHD (FIG. 5).

Discussion

We have developed a novel device to directly remove water from a CNS, e.g., a spinal or a brain tissue, in a controlled fashion to treat CNS or cerebral edema. The invention provides a HFHD for removing water from in vivo tissues, as validated using ex vivo tissue samples. Second, in the studies reported here, we validated the use of the exemplary HFHD of the invention, with the correct lumen solution properties, in conjunction with a craniectomy for enhancing survival in mice in vivo following cytotoxic cerebral edema. Third, we demonstrated that the HFHD is able to remove water from brain tissue and normalize CNS (brain) tissue water content.

Device design: Developing a HFHD to treat cerebral edema presents several technical challenges.

First, lumen solution and concentration need to be selected carefully. Although there are many possibilities for the lumen solution, we chose to use BSA in a CSF solution at physiological pH. BSA was chosen because its physical properties are known and because at high solution concentrations, it exhibits high osmotic pressure effects with moderate viscosity increases.[15,16]

Second, contact with the brain tissue and the liquid-liquid interface, if not maintained, could severely limit the removal of water and success of the treatment. In order to better maintain the liquid-liquid interface and contact with the brain tissue, we utilized a hydrogel. One advantage of the hydrogel is that it allows for the exemplary HFHD to conform to brain sulci and gyri. The moldability of the hydrogel will be a significant advantage.

Third, another design parameter of importance is the flexibility of the hollow fibers. We carefully chose very flexible hollow fibers so as to allow moldability through smaller openings in future applications (e.g. application through a burr hole and obviating the need for craniectomy).

The components of the exemplary HFHD allow for easy scale up. The number of the hollow fibers can be increased to increase treatment area to the maximum desired surface area. In alternative embodiments, a larger hydrogel can be used to cover a desired surface area. Further, increasing the amount of hollow fibers will allow for the HFHD to fully conform to the brain surface topography, including brain gyrations.

Device efficacy: In the present study, use of the exemplary HFHD of the invention to treat induced cytotoxic edema resulted in markedly improved survival compared to no treatment or craniectomy only. These results provide proof-of-principle for direct controlled water extraction as a novel form of treatment for cerebral edema. The device-brain surface contact is gentle and simple application of the device is not associated with any histological damage.

One important finding is that device application to one small quadrant of the brain over the right hemisphere (based on atlas calculations, we estimated contact of the device with approximately 17% of cortical surface area on the right hemisphere only) led to uniform reduction in water content throughout the brain and even in the contralateral hemisphere. These results suggest that even for large areas of hemispheric edema the area of contact may not need to be so extensive to attain adequate water extraction. This interesting result is likely due to rapid osmotic water flux via aquaporin-rich astrocyte networks[14] which will be investigated in future studies.

Study limitations and possible implications for treatment: While this study used a model of "pure" cytotoxic edema (water intoxication), in alternative embodiments, devices of the invention also can be used for post-stroke edema (which is thought to be largely cytotoxic in nature), brain tumor edema and post-infectious edema (these two are largely vasogenic in nature), and posttraumatic edema (which is mixed cytotoxic and vasogenic in nature).[9] Therefore, in alternative embodiments, devices of the invention are used to treat vasogenic edema and posttraumatic edema, and any type of cerebral edema. For example, in alternative embodiments, devices of the invention are used to treat "malignant" cerebral edema that cannot be adequately treated by other methods, including osmolar therapy, ventriculostomy, craniectomy only. In alternative embodiments the flexibility of application and titratability of duration of contact and rate of water removal are all user-defined parameters that can be tailored to a given clinical situation.

Conclusions

In summary, we have validated the use of an exemplary HFHD directly applied to the brain surface to treat and reverse severe cerebral edema. This therapy improved survival and reduced elevated brain tissue water content. In alternative embodiments, devices of the invention are used to treat e.g. any cerebral edema, such as controlled cortical impact (CCI), a model of traumatic brain injury. In alternative embodiments, devices of the invention are used flexibly to treat any anatomic extent and severity of edema given that the appropriate device parameters (lumen solution and concentration, flow rate, contact surface area) are chosen to provide the therapeutically appropriate water removal rate.

Figure Legends

FIG. 1: Concept of an exemplary hollow fiber-hydrogel device of the invention for treating a cerebral edema.

In alternative embodiments, aqueous proteinaceous solution is flowed or pumped or passively flowed across the edematous, e.g., a burned or an injured, area through the semi-permeable hollow fiber membrane lumen. The membrane is selected such that it completely rejects the solute but allows easy passage of ions, electrolytes and water, and also nutrients (such as oxygen or glucose) and small molecules, proteins and other drugs. The lumen solution induces an osmotic pressure driving force for water removal. The rate of pumping is controlled to allow fluid from the tissue to flow up into the membrane device due to osmotic pressure. In alternative embodiments, a hydrogel or an equivalent gel (e.g., a hydrophilic gel) with significantly large permeability is used to maintain membrane-tissue contact.

FIG. 9. Application of an exemplary hollow fiber-hydrogel device.

The left image of FIG. 9 illustrates an exemplary hollow fiber attached to inlet and outlet ports (of an exemplary device of the invention; and the right image of FIG. 9 illustrates application of an exemplary device with multiple parallel hollow fibers embedded in hydrogel to brain surface. Point A is the inlet of the fiber bundle. Point B is the gel that is placed directly on the tissue surface at the injury location. As can be seen, the gel also molds around the fiber bundle. Point C is the outlet for the fiber bundle. Fluid passing through the fiber at Point A osmotically drives excess fluid from the tissue under the gel at Point B into the walls of the hollow fibers. The excess fluid associated with edema is subsequently carried away from the brain at Point C.

FIG. 10. Hollow fiber-hydrogel device improves survival in a mouse model of cytotoxic cerebral edema.

Figure 10A:
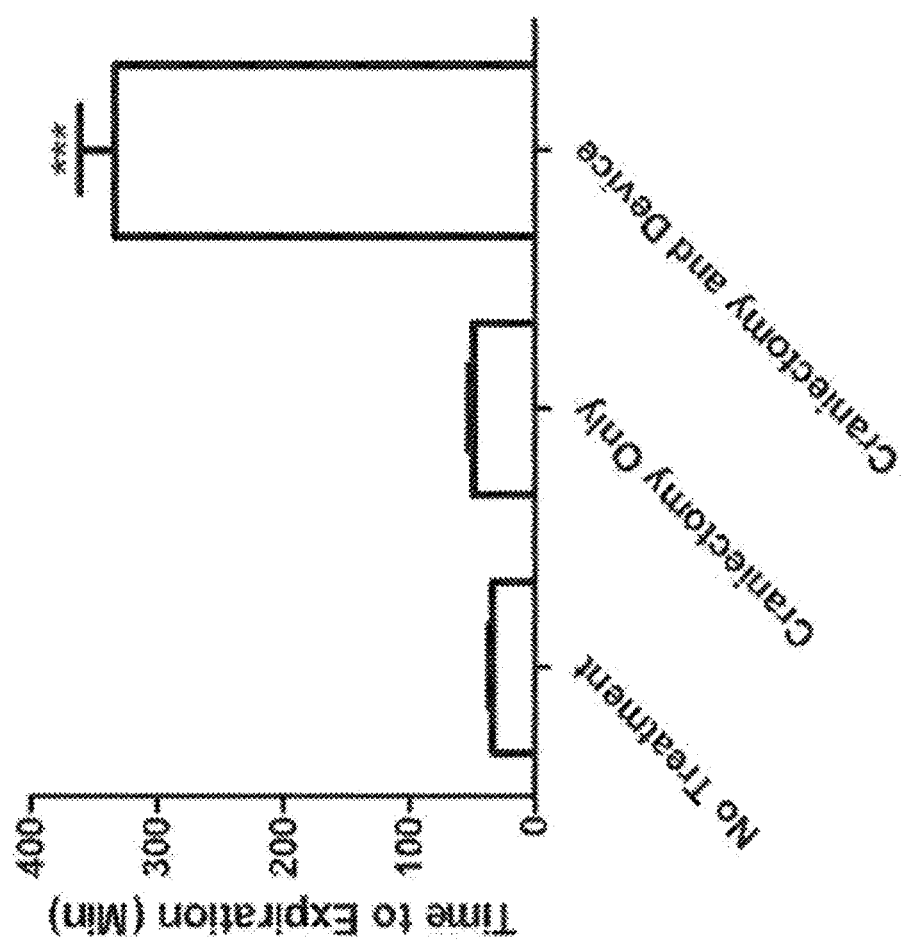
FIG. 10A graphically illustrates the time to expiration (min.) for three treatment groups, measuring no treatment (control), craniectomy (control) and craniectomy with the exemplary hollow fiber-hydrogel device of the invention as a function of time to expiration of the animal.
Figure 10B:
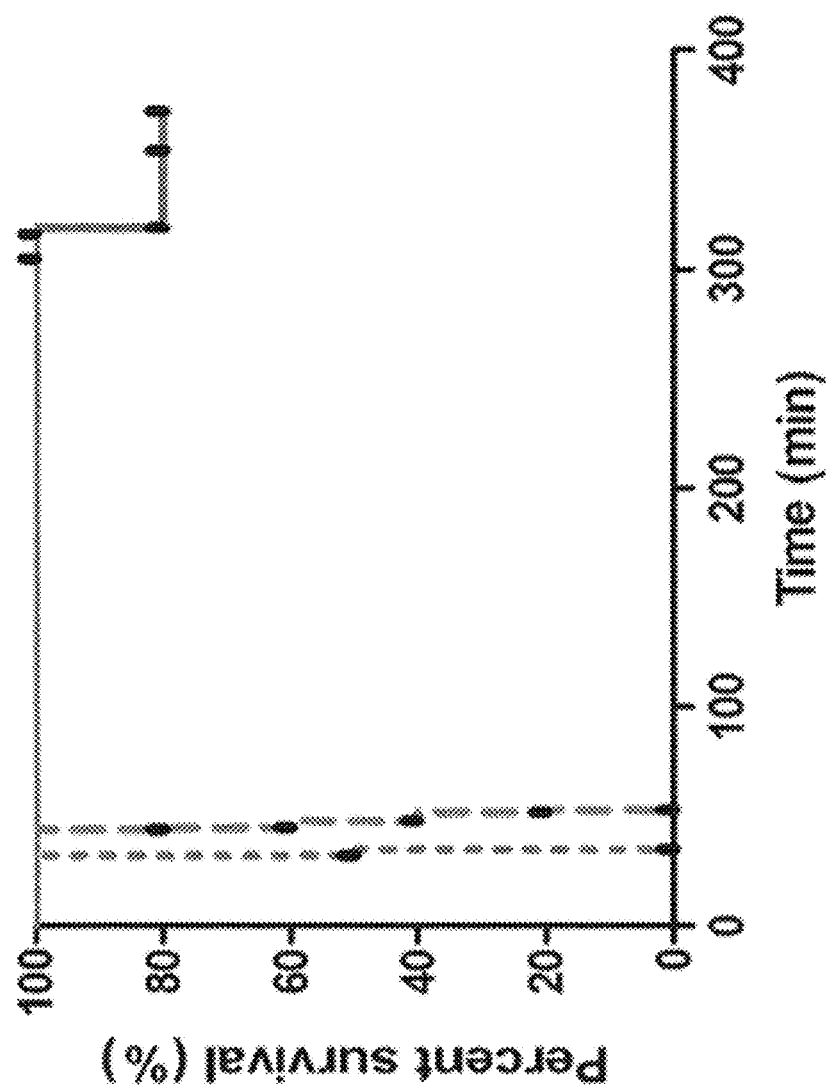
FIG. 10B (FIG. 11/14) graphically illustrates a Kaplan-Meier survival curve of percent (%) survival over time (minutes, min.); as discussed in detail, below.

FIG. 10A. Time to expiration (min.) for three treatment groups. W, water-intoxicated mice with no treatment (time to expiration: 31±3.1 min) W+C, water-intoxicated mice treated with craniectomy only (time to expiration: 48±4 min) W+C+D, water-intoxicated mice treated with craniectomy and HFHD (time to expiration: 333±28 min) Significant increase in time to expiration was seen in the mice treated with HFHD (***, p<0.001 vs. W or W+C groups). FIG. 10B. Kaplan-Meier survival curve. Comparison of the survival curves for W, W+C, and W+C+D groups. Individual mice are depicted as closed ovals.

Figure 11:
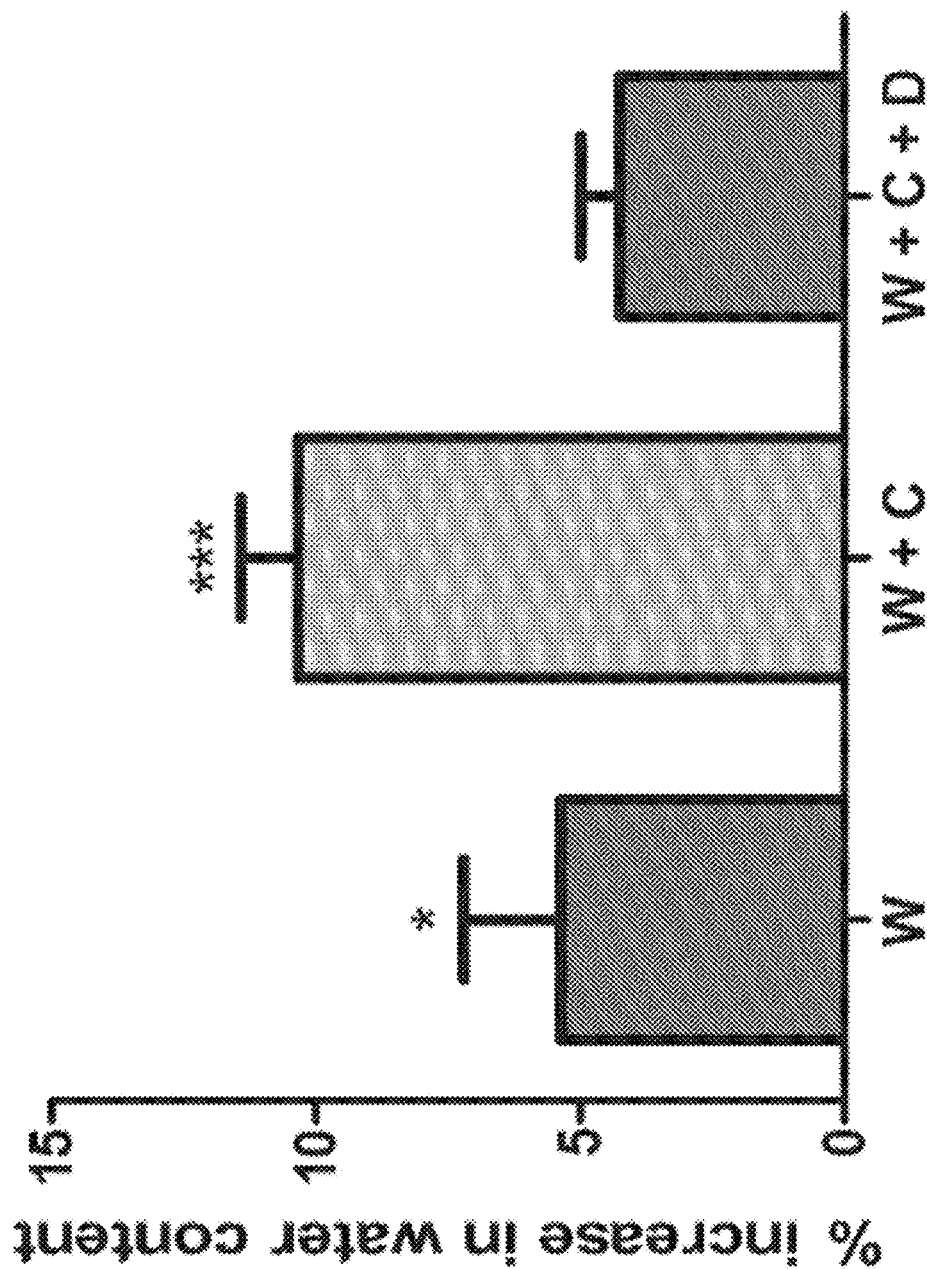
FIG. 11 (FIG. 12/14) and FIG. 12 (FIGS. 13/14 and 14/14) graphically illustrate the effectiveness of a hollow fiber-hydrogel device of the invention in limiting the increase in brain tissue water content.

FIG. 11 and FIG. 12. Hollow fiber-hydrogel device limits increase in brain tissue water content.

FIG. 11: Percent (%) increase in brain water content is shown for water-intoxicated mice with no treatment (W), water-intoxicated mice treated with craniectomy only (W+C), and water-intoxicated mice treated with craniectomy+HFHD (W+C+D). The % increase in brain water content was determined by subtracting the water content of the control animals (64.2±1.4%) The percent increase in brain water content of untreated water-intoxicated mice was significantly higher than control mice (*, p<0.05). The percent increase in brain water content of water-intoxicated mice treated with craniectomy only was significantly higher than that of control mice (***, p<0.001), untreated water-intoxicated animals (p<0.05), and water-intoxicated mice treated with craniectomy+HFHD (p<0.05). The percent increase in brain water content of water-intoxicated mice treated with craniectomy+HFHD was higher but not statistically significantly different from control mice.

Figure 12A:
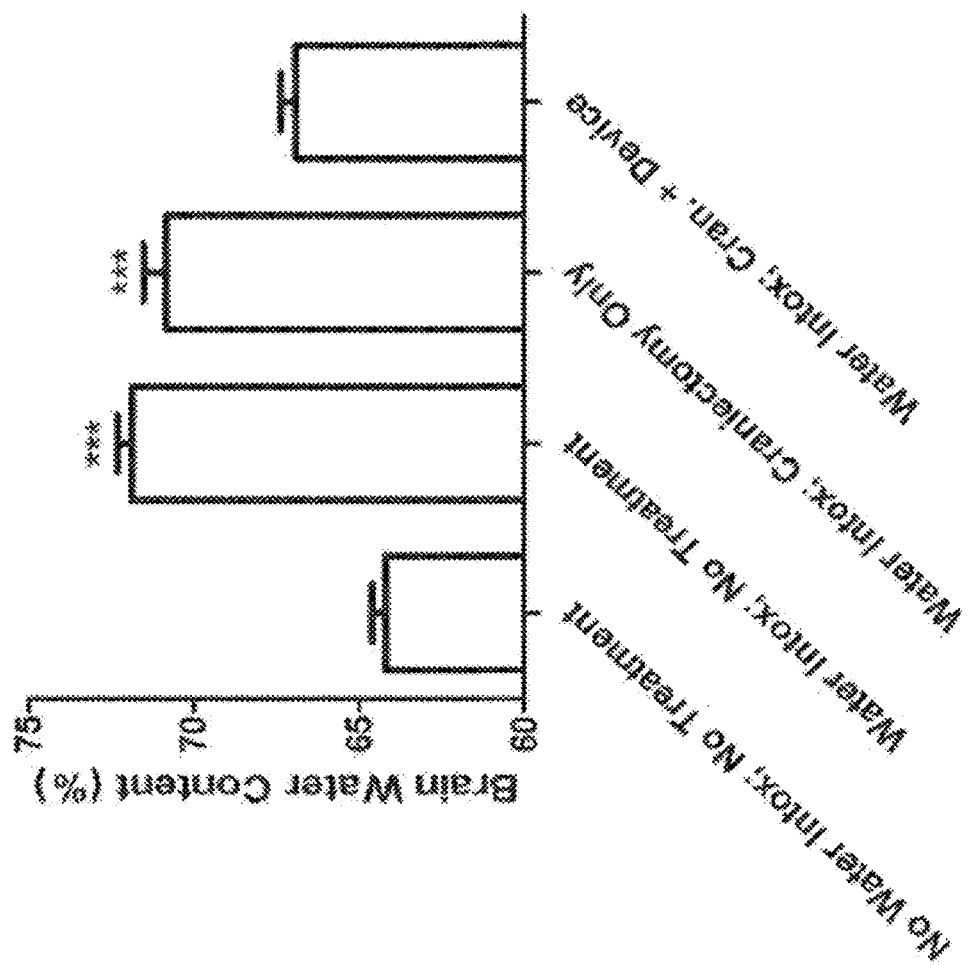
FIG. 12A graphically illustrates the percent (%) increase in brain water content is shown for water-intoxicated mice with no treatment (W), water-intoxicated mice no treatment, water-intoxicated craniectomy only ("C"), and water-intoxicated mice treated with craniectomy+HFHD (W+C+D); and, FIG. 12B graphically illustrates the percent (%) increase in brain water content, as is shown for no water-intoxicated mice with no treatment (W), no water and treated with craniectomy only (C), craniectomy only ("C"), and no water-intoxication with the exemplary device of the invention only, the "HFHD" ("D"); as discussed in detail, below.

FIG. 12A: Percent (%) increase in brain water content is shown for water-intoxicated mice with no treatment (W), water-intoxicated mice no treatment, water-intoxicated craniectomy only ("C"), and water-intoxicated mice treated with craniectomy +HFHD (W+C+D).

Figure 12B:
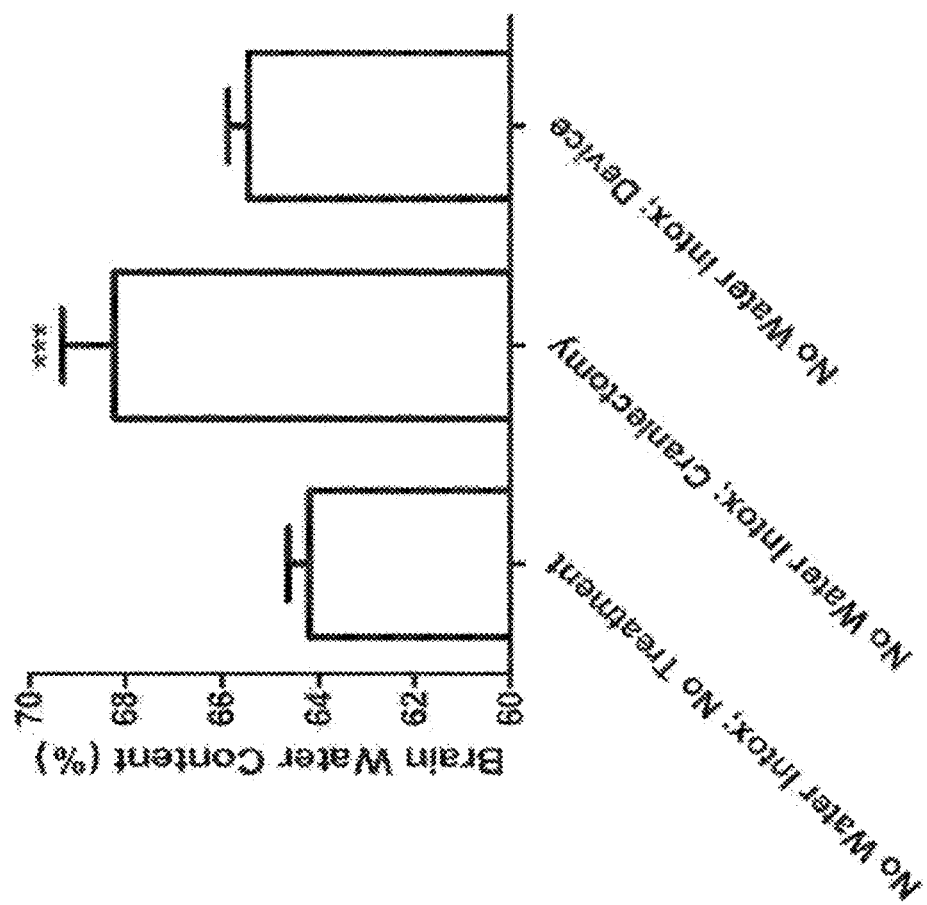

FIG. 12B: Percent (%) increase in brain water content is shown for no water-intoxicated mice with no treatment (W), no water and treated with craniectomy only (C), craniectomy only ("C"), and no water-intoxication with the exemplary device of the invention only, the "HFHD" ("D").

REFERENCES-EXAMPLE 1

1. Bingaman W E, Frank J I: Malignant cerebral edema and intracranial hypertension. Neurol Clin 13:479-509, 1995
2. Castillo L B, Bugedo G A, Paranhos J L: Mannitol or hypertonic saline for intracranial hypertension? A point of view. Crit Care Resusc 11:151-154, 2009
3. Cooper D J, Rosenfeld T V, Murray L, Arabi Y M, Davies A R, D'Urso P, et al: Decompressive craniectomy in diffuse traumatic brain injury. N Engl J Med 364:1493-1502, 2011
4. Csenkér É, Dioszeghy P, Fekete I, Mechler F: Ion concentrations in serum and cerebrospinal fluid of patients with neuromuscular diseases. Arch Psychiatr Nervenkr 231:251-258, 1982
5. Gill A S, Rajneesh K F, Owen C M, Yeh J, Hsu M, Binder D K: Early optical detection of cerebral edema in vivo. J Neurosurg 114:470-477, 2011
6. Hariri R J: Cerebral edema. Neurosurg Clin N Am 5:687-706, 1994
7. Kettenmann H, Ransom B R: Neuroglia, ed 2. London: Oxford University Press, 2005
8. Keyrouz G H, Dhar R, Diringer M N: Variation in osmotic response to sustained mannitol administration. Neurocrit. Care 9:204-209, 2008
9. Marmarou A: Pathophysiology of traumatic brain edema: current concepts. Acta Neurochir Suppl 86:7-10, 2003
10. Rabinstein A A: Treatment of cerebral edema. Neurologist 12:59-73, 2006
11. Schwarz S, Georgiadis D, Aschoff A, Schwab S: Effects of hypertonic (10%) saline in patients with raised intracranial pressure after stroke. Stroke 33:136-140, 2002
12. Suarez J I, Qureshi A I, Bhardwaj A, Williams M A, Schnitzer M S, Mirski M, et al: Treatment of refractory intracranial hypertension with 23.4% saline. Crit Care Med 26:1118-1122, 1998
13. Timofeev I, Dahyot-Fizelier C, Keong N, Nortje J, Al-Rawi P G, Czosnyka M, et al: Ventriculostomy for control of raised ICP in acute traumatic brain injury. Acta Neurochir Suppl 102:99-104, 2008
14. Verkman A S, Binder D K, Bloch 0, Auguste K, Papadopoulos M C: Three distinct roles of aquaporin-4 in brain function revealed by knockout mice. Biochim Biophys Acta, 2006
15. Vilker V L, Colton C K, Smith K A: The osmotic pressure of concentrated protein solutions: effect of concentration and pH in saline solutions of bovine serum albumin. Journal of Colloid and Interface Science 79:548-566, 1981
16. Yousef M A, Datta R, Rodgers V G J: Understanding non-idealities of the osmotic pressure of concentrated bovine serum albumin. Journal of Colloid and Interface Science 207:273-282, 1998
17. Zweckberger K, Eros C, Zimmermann R, Kim S W, Engel D, Plesnila N: Effect of early and delayed decompressive craniectomy on secondary brain damage after controlled cortical impact in mice. J Neurotrauma 23:1083-1093, 2006

REFERENCES

1. Desmoulin G T, Dionne J-P, "Blast-Induced Neurotrauma: Surrogate Use, Loading Mechanisms, and Cellular Responses", *J. Trauma: Inj., Infect., Crit. Care* 67(5): 1113-1122 (2009).
2. Kettenmann H, Ransom B R (2005) *Neuroglia* (Oxford University Press, London) 2nd Ed.
3. Marmarou A, "Pathophysiology of traumatic brain edema: current concepts", *Acta Neurochir Suppl* 86:7-10 (2003).
4. Park E, Bell J D, Baker A J, "Traumatic brain injury: Can the consequences be stopped?", *CMAJ* 178:1163-1170 (2008).
5. Rodgers V G J, Sparks R E, "Reduction of Membrane Fouling in the Ultrafiltration of Binary Protein Mixtures", *AIChE Journal*, 37(10): 1517-1528 (1991).
6. Rodgers V G J, Sparks R E, "Effect of Transmembrane Pressure Pulsing on Concentration Polarization", *Journal of Membrane Science*, 68:149-168, (1992)
7. Kedem O and Katchalsky A, "Thermodynamic Analysis of the Permeability of Biological Membranes to Non-Electrolytes", *Biochim. Biophys. Acta.*, 27:229-246 (1958).
8. Yousef M A, Datta R, and Rodgers V G J, "Free-Solvent Model of Osmotic Pressure Revisited. Application to Concentrated IgG Solution at Physiological Conditions", *Journal of Colloid and Interface Science*, 197:108-118 (1998).
9. Yousef M A, Datta R, Rodgers V G J, "Understanding Non-Idealities of the Osmotic Pressure of Concentrated Bovine Serum Albumin", *Journal of Colloid and Interface Science*, 207(2):273-282 (1998).

10. Yousef M A, Datta R, Rodgers V G J, "Monolayer Hydration Governs Nonideality in Osmotic Pressure of Protein Solutions", *AIChE Journal*, 48(6):1301-1308 (2002).

11. Yousef M A, Datta R, Rodgers V G J, "Model of Osmotic Pressure for High Concentrated Binary Protein Solutions", *AIChE Journal*, 48(4):913-917 (2002).

12. Wang Y, Rodgers V G J, "Free-Solvent Model Shows Osmotic Pressure is the Dominant Factor in Limiting Flux during Protein Ultrafiltration", *Journal of Membrane Science*, 320:335-343 (2008).

13. Wang Y, Rodgers V G J, "Critical Flux in Protein Ultrafiltration: a New Definition through the Free-Solvent-Based (FSB) Model", *AIChE Journal*, in press, doi: 10.1002/aic.12152 (2010).

14. Keyrouz G H, Dhar R, Diringer M N, "Variation in osmotic response to sustained mannitol administration." *Neurocrit. Care* 9:204-209 (2008).

15. Castillo L B, Bugedo G A, Paranhos J L, "Mannitol or hypertonic saline for intracranial hypertension? A point of view." *Crit Care Resusc.* 11:151-154 (2009)

16. Czosnyka M, Pickard J D, "Monitoring and interpretation of intracranial pressure." *J Neurol Neurosurg Psychiatry* 75:813-821 (2004).

17. Marmarou A, Poll W, Shulman K, Bhagavan H, "A simple gravimetric technique for measurement of cerebral edema." *J Neurosurg* 49:530-537 (1978).

18. Gill A S, Rajneesh K F, Owen C M, Yeh J, Hsu M and Binder D K, "Early optical detection of cerebral edema in vivo." *J Neurosurg.* [Mar. 5 Epub ahead of print] (2010).

19. Box, G E, Hunter W G, Hunter J S, *Statistics for Experimenters*, J. Wiley & Sons, New York, N.Y. (1978).

20. Waypole, R E, Myers R H, *Probability and Statistics for Engineers and Scientists*, 4$^{th}$ ed., Macmillan Publishing Co., New York, N.Y. (1989).

21. Csenkér É, Diószeghy P, Fekete I, Mechler F, "Ion Concentrations in Serum and Cerebrospinal Fluid of Patients with Neuromuscular Diseases", *Arch Psychiatr Nervenkr*, 231:251-258 (1982).

22. Tanford C, *Physical Chemistry of Macromolecules*, J. Wiley & Sons (1961).

23. Aune K C, Tanford C, "Thermodynamics of the Denaturation of Lysozyme by Guanidine Hydrochloride. I. Dependence on pH at 25° C.", *Biochemistry*, 8(11): 4579-4585 (1969).

24. Abe Y, Ueda T, Iwashita H, Hashimoto Y, Motoshima H, Tanaka Y, Imoto T, "Effect of Salt Concentration on the $pK_a$ of Acidic Residues in Lysozyme", *Biochem.* (Tokyo) 118(5), 946-952 (1995).

25. Tanford C, Swanson S A, Shore W S, "Hydrogen Ion Equilibria of Bovine Serum Albumin", *J. Am. Chem. Soc.*, 77:6414-6421 (1955).

26. Bailey S, Evans R W, Garratt R C, Gorinsky B, Hasnain S, Horsburgh C, Jhoti H, Lindley P F, Mydin A, Sarra R, et al., "Molecular Structure of Serum Transferrin at 3.3-A Resolution", *Biochemistry*, 27(15):5804-5812 (1988).

27. Roberts R, Makey D G, Seal U S, "Human Transferrin. Molecular Weight and Sedimentation Properties", *J. Biol. Chem.*, 241(21):4907-4913 (1966).

28. Princiotto J V, Zapolski E J, "Transferrin", *Nature*, 229(5284):435 (1971).

29. Baker E N, Anderson B F, Baker H M, Haridas M, Jameson G B, Norris G E, Rumball S V, Smith C A, "Structure, Function and Flexibility of Human Lactoferrin", *Int. J Biol. Macromol.*, 13(3):122-129 (1991).

30. Moore S A, Anderson B F, Groom C R, Haridas M, Baker E N, "Three-Dimensional Structure of Diferric Bovine Lactoferrin at 2.8 Å Resolution", *J. Mol. Biol.*, 274(2):222-236 (1997).

31. Creighton T E, *Proteins: Structure and Molecular Properties*, 2$^{nd}$ Ed., W. H. Freeman and Co., N Y (1993).

32. Kanehisa M I, Ikegami A, "Structural Changes and Fluctuations of Proteins. I I. Analysis of the Denaturation of Globular Proteins", *Biophys. Chem.*, 6(2):131-149 (1977).

33. Yang A S, Honig B, "On the pH Dependency of Protein Stability", *J. Mol. Biol.*, 231(2):459-474 (1993).

34. Lapanje S, *Physiochemical Aspects of the Proteins Denaturation*, Wiley-Interscience Publications, N Y (1978).

35. Tanford C, "Protein Denaturation", *Adv. Protein Chem.*, 23:121-282 (1968).

36. Papadopoulos M C, Binder D K and Verkman A S. "Enhanced macromolecular diffusion in brain extracellular space in mouse models of vasogenic edema measured by cortical surface photobleaching." *FASEB J.* 3:425-427 (2005).

37. Tait M J, Saadoun S, Bell B A, Verkman A S and Papadopoulos M C. "Increased brain edema in AQP4-null mice in an experimental model of subarachnoid hemorrhage." *Neuroscience* 167:60-67 (2010).

38. Huang D, Swanson E A, Lin C P, Schuman J S, Stinson W G, Chang W, Hee M R, Flotte T, Gregory K, Puliafito C A, Fujimoto J G Optical coherence tomography, *Science*, 254:1178 (1991).

39. Andretzky, P., Lindner, M. W., Hermann, J. M., Schultz, A., Konzog, M., Klesewetter, F. & Hausler, G. Optical coherence tomography by spectral radar. *Proceedings of the SPIE*, 3567:78(1998).

40. Mitsui T, "Dynamic range of optical reflectometry with spectral interferometry." *Japanese Journal of Applied Physics Part I—Regular Papers Short Notes & Review Papers*, 38:6133 (1999).

41. Leitgeb R, Hitzenberger C K, Fercher A F, "Performance of Fourier domain versus time domain optical coherence tomography." *Optics Express* 11:889 (2003).

42. de Boer J F, Cense B, Park B H, Pierce M C, Tearney G J, Bouma B E "Improved signal-to-noise ratio in spectral-domain compared with time-domain optical coherence tomography." *Optics Letters* 28:2067 (2003).

43. Choma M A, Sarunic M V, Yang C H, Izatt J A, "Sensitivity advantage of swept source and Fourier domain optical coherence tomography." *Optics Express* 11:2183 (2003).

44. Park B H, Pierce M C, Cense B, Yun S H, Mujat M, Tearney G J, Bouma B E, de Boer J F, "Real-time fiber-based multi-functional spectral-domain optical coherence tomography at 1.3 μm." *Optics Express*, 13(11):3931-3944 (2005).

45. Pierce M C, Shishkov M, Park B H, Nassif N A, Bouma B E, Tearney G J, de Boe J F, "Effects of sample arm motion in endoscopic polarization-sensitive optical coherence tomography." *Optics Express*, 13:5739 (2005).

46. Ki K H, Park B H, Maguluri G N, Lee T, Rogomentich F, Bancu M, Bouma B E, de Boer J F, Bernstein J J, "Two-axis magnetically driven MEM scanning catheter for endoscopic high-speed optical coherence tomography." *Optics Express*, 15(26):18130-18140 (2007).

47. Schmitt J M, Knuttel A, Bonner R F, "Measurement of optical properties of biological tissues by low-coherence reflectometry." *Applied Optics*, 32:6032 (1993).

48. Knuttel A, Boehlau-Godau M, "Spatially confined and temporally resolved refractive index and scattering evaluation in human skin performed with optical coherence tomography." *Journal of Biomedical Optics*, 5:83 (2000).

A number of embodiments of the invention have been described. Nevertheless, it will be understood that various modifications may be made without departing from the spirit and scope of the invention. Accordingly, other embodiments are within the scope of the following claims.

What is claimed is:

1. A method for removing water from a traumatically injured central nervous system (CNS) tissue in a subject in a controlled fashion, the method comprising:
    exposing a surface of the traumatically injured CNS tissue;
    applying agar to the exposed surface of the traumatically injured CNS tissue, wherein the agar is permeable and allows passage of water, and wherein the agar conforms to the tissue to maximize contact area with the tissue,
    placing a hollow fiber membrane in contact with the agar, wherein the hollow fiber membrane comprises a semi-permeable membrane having a molecular weight cut-off of between about 1 to 60 kilodaltons (kDa) and a lumen; and
    flowing or pumping through the lumen a concentrated solution of a globular protein that produces a concentration-dependent osmotic pressure, wherein the globular protein cannot pass through the semi-permeable membrane, wherein the concentrated solution of the globular protein in the hollow fiber induces an osmotic pressure that draws water from the tissue into the agar and then into the hollow fiber membrane, where the water is removed and carried away from the agar and the tissue.

2. The method according to claim 1, wherein the globular protein is bovine serum albumin (BSA).

3. The method according to claim 1, wherein the hollow fiber membrane comprises a material selected from the group consisting of polynephron, polyflux, polysulfone and regenerated cellulose.

4. The method according to claim 1, wherein the hollow fiber membrane is regenerated cellulose and the globular protein is BSA.

5. The method according to claim 2, wherein the BSA is at a concentration of about 350 g/l.

6. The method according to claim 1, wherein the CNS tissue is a spinal tissue or a brain tissue.

7. The method according to claim 1, wherein the hollow fiber membrane is embedded within the agar.

8. The method according to claim 1, wherein a rate of flowing or pumping of the concentrated solution through the semi-permeable hollow fiber membrane is controlled to allow fluid from the tissue to flow up to the membrane device due to osmotic pressure.

9. The method according to claim 1, wherein the hollow fiber conforms to the surface of the traumatically injured CNS tissue.

10. The method according to claim 1, wherein an amount of the globular protein that cannot pass through the semi-permeable membrane is changed or modified to alter the rate of water removal.

11. The method according to claim 1, wherein a concentration of the globular protein that cannot pass through the semi-permeable membrane is altered to between about 0.1 to about 50% to alter the rate of water removal.

12. The method according to claim 1, wherein the temperature of the concentrated solution is changed in the range of about 20° C. to about 37° C. to alter the rate of water removal.

13. The method according to claim 1, wherein the molecular weight cut-off of the semipermeable membrane of the hollow fiber membrane is between about 1 to 30 kDa.

14. The method according to claim 1, wherein the traumatically injured central nervous system (CNS) tissue is brain tissue and the surface of the traumatically injured CNS tissue is exposed by craniotomy or craniectomy.

* * * * *